US008536114B2

(12) United States Patent
Li et al.

(10) Patent No.: US 8,536,114 B2
(45) Date of Patent: Sep. 17, 2013

(54) MACROCYCLES

(75) Inventors: Keqiang Li, Cary, NC (US); David Renwick Houck, Cary, NC (US); Cyprian Okwara Ogbu, Durham, NC (US); Michael Robert Peel, Research Triangle Park, NC (US); Andrew William Scribner, Durham, NC (US)

(73) Assignee: Scynexis, Inc., Durham, NC (US)

( * ) Notice: Subject to any disclaimer, the term of this patent is extended or adjusted under 35 U.S.C. 154(b) by 698 days.

(21) Appl. No.: 12/650,096

(22) Filed: Dec. 30, 2009

(65) Prior Publication Data

US 2010/0173836 A1 Jul. 8, 2010

Related U.S. Application Data

(60) Provisional application No. 61/142,068, filed on Dec. 31, 2008.

(51) Int. Cl.
*A61K 38/00* (2006.01)
*C07K 7/50* (2006.01)
*A61P 31/12* (2006.01)

(52) U.S. Cl.
USPC .......................................... 514/1.1; 530/317

(58) Field of Classification Search
None
See application file for complete search history.

(56) References Cited

U.S. PATENT DOCUMENTS

| | | | |
|---|---|---|---|
| 4,703,033 A | 10/1987 | Sebach | |
| 4,771,122 A | 9/1988 | Sebach | |
| 4,798,823 A | 1/1989 | Witzel | |
| 4,814,323 A | 3/1989 | Andrieu et al. | |
| 4,885,276 A | 12/1989 | Witzel | |
| 4,996,193 A | 2/1991 | Hewitt et al. | |
| 5,294,604 A | 3/1994 | Nussenblatt | |
| 5,639,852 A | 6/1997 | Rich et al. | |
| 5,846,964 A | 12/1998 | Ozeki | |
| 5,863,550 A | 1/1999 | Maeda et al. | |
| 5,948,693 A | 9/1999 | Rich et al. | |
| 5,948,755 A | 9/1999 | Barriere et al. | |
| 5,948,884 A | 9/1999 | Lüchinger | |
| 5,965,527 A * | 10/1999 | Barriere et al. | 514/2.4 |
| 5,977,067 A | 11/1999 | Evers et al. | |
| 5,981,479 A | 11/1999 | Ko et al. | |
| 5,994,299 A | 11/1999 | Barriere et al. | |
| 6,254,860 B1 | 7/2001 | Garst | |
| 6,350,442 B2 | 2/2002 | Garst | |
| 6,444,643 B1 | 9/2002 | Steiner et al. | |
| 6,521,595 B1 | 2/2003 | Kim et al. | |
| 6,583,265 B1 | 6/2003 | Ellmerer-Müller et al. | |
| 6,924,271 B2 | 8/2005 | Averett et al. | |
| 6,927,208 B1 | 8/2005 | Wenger | |
| 7,196,161 B2 * | 3/2007 | Fliri et al. | 530/317 |
| 7,226,905 B2 | 6/2007 | Viskov | |
| 7,576,057 B2 | 8/2009 | Scribner et al. | |
| 7,718,767 B2 | 5/2010 | Fliri et al. | |
| 7,754,685 B2 | 7/2010 | Houck | |
| 8,188,052 B2 | 5/2012 | Houck | |
| 2004/0077587 A1 | 4/2004 | Sommadossi et al. | |
| 2004/0087496 A1 | 5/2004 | Kim et al. | |
| 2004/0254117 A9 | 12/2004 | Saksena et al. | |
| 2006/0089301 A1 | 4/2006 | Fliri et al. | |
| 2006/0160727 A1 * | 7/2006 | Fliri et al. | 514/11 |
| 2007/0173440 A1 | 7/2007 | Houck | |
| 2007/0275884 A1 | 11/2007 | Hijikata et al. | |
| 2008/0171699 A1 | 7/2008 | Scribner et al. | |
| 2008/0255038 A1 | 10/2008 | Hopkins et al. | |
| 2009/0298751 A1 | 12/2009 | Houck et al. | |
| 2009/0306033 A1 | 12/2009 | Li et al. | |
| 2009/0312300 A1 | 12/2009 | Li et al. | |
| 2010/0062975 A1 | 3/2010 | Houck | |
| 2010/0167996 A1 | 7/2010 | Fliri et al. | |
| 2010/0173836 A1 | 7/2010 | Li et al. | |
| 2010/0173837 A1 | 7/2010 | Hopkins | |
| 2010/0227801 A1 | 9/2010 | Hopkins | |
| 2011/0144005 A1 | 6/2011 | Li et al. | |

FOREIGN PATENT DOCUMENTS

| | | |
|---|---|---|
| CN | 1305493 A | 7/2001 |
| EP | 0484281 B2 | 11/2000 |
| WO | 97/04005 A2 | 2/1997 |
| WO | WO 98/28328 A1 | 7/1998 |

(Continued)

OTHER PUBLICATIONS

S.R. Vippagunta, et al. Adv. Drug Delivery Rev. (2001) 48, pp. 3-26).*
EPO Supplemental European Search Report, dated Jul. 18, 2008, for European Application No. EP 05815625.8, filed Sep. 30, 2005.
EPO European Examination Report, Communication pursuant to Article 94(3) EPC, dated Sep. 8, 2008, for European Application No. EP 06816230.4, filed Oct. 2, 2006.

(Continued)

*Primary Examiner* — Suzanne Ziska
(74) *Attorney, Agent, or Firm* — Jones Day

(57) ABSTRACT

Disclosed herein are compounds of general formula (I):

(I)

wherein A, B, $R^1$ and $R^2$ are as defined in the specification, and their use as pharmaceuticals.

13 Claims, No Drawings

(56) References Cited

FOREIGN PATENT DOCUMENTS

| | | |
|---|---|---|
| WO | WO 98/28329 A1 | 7/1998 |
| WO | WO 98/28330 A1 | 7/1998 |
| WO | WO 98/49193 A1 | 11/1998 |
| WO | WO 99/32512 A1 | 7/1999 |
| WO | WO 99/62540 A1 | 12/1999 |
| WO | WO 99/65933 A1 | 12/1999 |
| WO | WO 99/67280 A1 | 12/1999 |
| WO | WO 00/01715 A1 | 1/2000 |
| WO | WO 01/47883 A1 | 5/2001 |
| WO | WO 2004/041221 A1 | 5/2004 |
| WO | WO 2004/072108 A1 | 8/2004 |
| WO | WO 2005/000308 A2 | 1/2005 |
| WO | WO 2005/021028 A1 | 3/2005 |
| WO | WO 2006/005580 A1 | 1/2006 |
| WO | WO 2006/005610 A1 | 1/2006 |
| WO | WO 2006/038088 A1 | 4/2006 |
| WO | WO 2006/039668 A2 | 4/2006 |
| WO | WO 2006/071618 A1 | 7/2006 |
| WO | WO 2006/071619 A1 | 7/2006 |
| WO | WO 2007/041631 A1 | 4/2007 |
| WO | WO 2007/041632 A2 | 4/2007 |
| WO | WO 2007/136759 A2 | 11/2007 |
| WO | WO 2008/069917 A2 | 6/2008 |
| WO | WO 2008/127613 A1 | 10/2008 |
| WO | WO 2008/143996 A1 | 11/2008 |
| WO | WO 2009/148615 A1 | 12/2009 |
| WO | WO 2010/002428 A2 | 1/2010 |
| WO | 2010/076329 A1 | 8/2010 |
| ZA | 98/11531 | 12/1998 |

OTHER PUBLICATIONS

ISA/US PCT International Search Report and Written Opinion dated Feb. 6, 2007, for International Application No. PCT/US05/35533, filed Sep. 30, 2005.

ISA/US PCT International Preliminary Report on Patentability dated Apr. 3, 2007, for International Application No. PCT/US05/35533, filed Sep. 30, 2005.

ISA/US PCT International Search Report and Written Opinion dated Jan. 19, 2007, for International Application No. PCT/US06/038822, filed Oct. 2, 2006.

ISA/US PCT International Preliminary Report on Patentability dated Apr. 1, 2008, for International Application No. PCT/US06/038822, filed Oct. 2, 2006.

ISA/US PCT International Search Report and Written Opinion dated Oct. 27, 2009, for International Application No. PCT/US09/003410, filed Jun. 5, 2009.

ISA/US PCT International Search Report dated Jan. 21, 2010, for International Application No. PCT/US09/003411, filed Jun. 5, 2009.

ISA/EP PCT International Search Report and Written Opinion dated May 6, 2010, for International Application No. PCT/EP09/068017, filed Dec. 30, 2009.

U.S.P.T.O. Nonfinal Office Action dated Oct. 2, 2006, in U.S. Appl. No. 11/241,650, filed Sep. 30, 2005.

U.S.P.T.O. Nonfinal Office Action dated Dec. 11, 2007, in U.S. Appl. No. 11/386,291, filed Mar. 21, 2006.

U.S.P.T.O. Nonfinal Office Action, dated Feb. 22, 2010, for U.S. Appl. No. 12/101,091, filed Apr. 10, 2008.

U.S.P.T.O. Issue Notification, dated Jun. 23, 2010, for U.S. Appl. No. 11/542,930, filed Oct. 2, 2006.

Baumgrass et al., 2004, "Substitution in Position 3 of Cyclosporin A Abolishes the Cyclophilin-mediated Gain-of-function Mechanism but Not Immunosuppression," *Journal of Biological Chemistry*, vol. 279(4):2470-2479.

Billich et al., 1995, "Mode of Action of SDZ NIM 811, a Nonimmunosuppressive Cyclosporin A Analog with Activity Against Human Immunodeficiency Virus (HIV) Type 1: Interference with HIV Protein-Cyclophilin A Interactions," *Journal of Virology*, vol. 69(4):2451-2461.

Biswal et al., 2005, "Crystal Structures of the RNA-dependent RNA Polymerase Genotype 2a of Hepatitis C Virus Reveal Two Conformations and Suggest Mechanisms of Inhibition by Non-Nucleoside Inhibitors," *J. Biol. Chem.*, vol. 280:18202-18210.

Borel et al., 1977, "Effects of the New Anti-Lymphocytic Peptide Cyclosporin A in Animals," *Immunology*, vol. 32:1017-1025.

Carry et al., 2004, "Semisynthetic Di- and Tri-Functionalized Non-Immunosuppressive Cyclosporin A Derivatives as Potential Anti-HIV 1 Drugs," *Synlett* No. 2:316-320.

Chan et al., 2004, "Discovery of Thiophene-2-Carboxylic Acids as Potent Inhibitors of HCV NS5B Polymerase and HCV Subgenomic RNA Replication. Part 1: Sulfonamides," *Bioorganic & Medical Chemistry Letters*, 14:793-796.

Chan et al., 2004, "Discovery of Thiophene-2-Carboxylic Acids as Potent Inhibitors of HCV NS5B Polymerase and HCV Subgenomic RNA Replication. Part 2: Tertiary Amides," *Bioorganic & Medicinal Chemistry Letters*, 14:797-800.

Cotler et al., 2003-2004, "A Pilot Study of the Combination of Cyclosporin A and Interferon Alfacon-1 for the Treatment of Hepatitis C in Previous Nonresponder Patients," *Journal of Clinical Gastroenterology*, vol. 36(4):352-355.

Debio Pharm Press Release, New Data Presented on Debiopharm's Debio-25 at the 11th International Symposium on Hepatitis C Virus and Related Viruses in Heidelberg, Germany, Oct. 6, 2004.

Dhanak et al., 2002, "Identification and Biological Characterization of Heterocyclic Inhibitors of the Hepatitis C Virus RNA-Dependent RNA Polymerase," *Journal of Biological Chemistry*, vol. 277(41):38322-38327.

DiMarco et al., 2005, "Interdomain Communication in Hepatitis C Virus Polymerase Abolished by Small Molecule Inhibitors Bound to a Novel Allosteric Site," *Journal of Biological Chemistry*, vol. 280(33):29765-29770.

Evers et al., 2003, "Synthesis of Non-Immunosuppressive Cyclophilin-Binding Cyclosporin A Derivatives as Potential Anti-HIV-1 Drugs," *Bioorganic & Medicinal Chemistry Letters*, vol. 13:4415-4419.

Gu et al., 2003, "Arresting Initiation of Hepatitis C Virus RNA Synthesis Using Heterocyclic Derivatives," *Journal of Biological Chemistry*, vol. 278(19):16602-16607.

Hansson et al., 2004, "The Nonimmunosuppressive Cyclosporin Analogs NIM811 and UNIL025 Display Nanomolar Potencies on Permeability Transition in Brain Derived Mitochondria," *Journal of Bioenergetics and Biomembranes*, vol. 36(4):407-413.

Horsmans et al., 2004, "Isatoribine, A Toll-Like Receptor 7 Agonist, Significantly Reduced Plasma Viral Load in a Clinical Proof-of-Concept Study in Patients with Chronic Hepatitis C Virus Infection," *Hepatology*, vol. 40:(4), Suppl. 1, Oct. 2004, 282A, No. 270.

Hubler et al., 2000, Synthetic Routes to NEtXaa4-Cyclosporin A Derivatives as Potential Anti-HIV I Drugs, *Tetrahedron Letters*, vol. 41(37):7193-7196.

Inoue et al., 2003, "Combined Interferon Alpha2b and Cyclosporin A in the Treatment of Chronic Hepatitis C: Controlled Trial," *Journal of Gastroenterology*, Springer Verlag, Tokyo, JP, vol. 38(6):567-572.

Inoue et al., 2005, "Interferon Combined with Cyclosporin Treatment as an Effective Countermeasure Against Hepatitis C Virus Recurrence in Liver Transplant patients with End-Stage Hepatitis C Virus Related Disease," *Transplantation Proceedings*, vol. 37(2):1233-1234.

Kallen et al., 1997, "12 Cyclosporins: Recent Developments in Biosynthesis, Pharmacology and Biology, and Clinical Applications," *Biotechnology*, 2nd Ed. Completely Revised Edition, vol. 7: 535-591.

LaMarre et al., 2003, "An NS3 Protease Inhibitor with Antiviral Effects in Humans Infected with Hepatitis C Virus," *Nature*, vol. 426:186-189.

LaPlante et al., 2004, "Binding Mode Determination of Benzimidazole Inhibitors of the Hepatitis C Virus RNA Polymerase by a Structure and Dynamics Strategy," *Angew. Chem. Int.*, Ed. Engl., vol. 32:4306-4311.

Lee et al., 2003, "Molecular Basis for the Immunostimulatory Activity of Guanine Nucleoside Analogs: Activation of Toll-Like Receptor 7," *PNAS*, USA, vol. 100(11):6646-6651.

Lin et al., 2005, "In Vitro Studies of Cross-Resistance Mutations Against Two Hepatitis C Virus Serine Protease Inhibitors, VX-950 and BILN 2061," *Journal of Biological Chemistry*, vol. 280(44):36784-36791.

Love et al., 2003, "Crystallographic Identification of a Noncompetitive Inhibitor Binding Site on the Hepatitis C Virus NS5B RNA Polymerase Enzyme," *Journal of Virology*, vol. 77(13):7575-7581.

Nakagawa et al., 2004, "Specific Inhibition of Hepatitis C Virus Replication by Cyclosporin A," *Biochem. Biophys. Res. Commun.*, vol. 313:42-47.

Nguyen et al., 2003, "Resistance Profile of a Hepatitis C Virus RNA-Dependent RNA Polymerase Benzothiadiazine Inhibitor," *Antimicrobial Agents and Chemotherapy*, vol. 47(11):3525-3530.

Olsen et al., 2004, "A 7-Deaza-Adenosine Analog is a Potent and Selective Inhibitor of Hepatitis C Virus Replication with Excellent Pharmacokinetic Properties," *Antimicrobial Agents and Chemotherapy*, vol. 48(10):3944-3953.

Peel et al., "The Discovery of Novel, Non-Immunosuppressive Cyclosporin Ethers, and Thioethers with Potent HCV Activity," AASLD Abstracts XP-002561933, *Hepatology*, vol. 48, No. 4, Suppl. S, Oct. 2008, p. 1167A, Abstract 1915.

Randall et al., 2003, "Clearance of Replicating Hepatitis C Virus Replicon RNAs in Cell Culture by Small Interfering RNAs," *PNAS*, vol. 100(1):235-240.

Ruegger et al., 1976, "Cyclosporin A, a Peptide Metabolite from *Trichoderma polysporum* (Link ex Pers.) *Rifai*, with a Remarkable Immunosuppressive Activity," *Helvetica Chimica Acta*, vol. 59(4): 1075-1092.

Schetter et al., 2004, "Toll-Like Receptors Involved in the Response to Microbial Pathogens: Development of Agonists for Toll-Like Receptor 9," *Current Opinion in Drug Discovery & Development*, vol. 7(2):204-210.

Shimotohno et al., 2004, "Inhibitory Role of Cyclosporin A and Its Derivatives on Replication of Hepatitis C Virus," American Transplant Congress, Abstract No. 648 (American Journal of Transplantation, 4(s8):1-653).

Simmonds, 2001, "The Origin and Evolution of Hepatitis Viruses in Humans," *Journal of General Virology*, vol. 82:693-712.

Simmonds, 2004, "Genetic Diversity and Evolution of Hepatitis C Virus—15 Years On," *Journal of General Virology*, vol. 85:3173-3188.

Summa, 2005, "VX-950 Vertex/Mitsubishi," *Current Opinion in Investigational Drugs*, vol. 6(8):831-837.

Takeda et al., 2003, "Toll-Like Receptors," *Annual Review Immunology*, vol. 21:335-376.

Tomei et al., 2004, "Characterization of the Inhibition of Hepatitis C Virus RNA Replication by NonNucleosides," *Journal of Virology*, vol. 78(2):938-946.

Traber et al., 1987, "Novel Cyclosporins from *Tolypocladium inflatum*. The Cyclosporins K-Z," *Helvetica Chimica Acta*, vol. 70(1):13-36.

Wang et al., 2003, "Non-Nucleoside Analogue Inhibitors Bind to an Allosteric Site on HCV NS5B Polymerase," *Journal of Biological Chemistry*, vol. 278(11):9489-9495.

Watashi et al., 2003, "Cyclosporin A Suppresses Replication of Hepatitis C Virus Genome in Cultured Hepatocytes," *Hepatology*, vol. 38:1282-1288.

Watashi et al., 2005, "Cyclophilin B is a Functional Regulator of Hepatitis C Virus RNA Polymerase," *Molecular Cell*, vol. 19:111-122.

Watashi et al., 2005, "Current Approaches for Developing New Anti-HCV Agents and Analyses of HCV Replication Using Anti-HCV Agents," *Uirusu*, vol. 55(1):105-110.

Whitby et al., 2004, "Action of Celgosivir (6 O-butanoyl castanospermine) Against the Pestivirus BVDV: Implications for the Treatment of Hepatitis C," *Antivir Chem Chemother.* vol. 15:141-151.

Xia et al., 2005, "Inhibitory Effect of Cyclosporine A on Hepatitis B Virus Replication in Vitro and its Possible Mechanisms," *Hepatobiliary & Pancreatic Diseases International*, vol. 4(1):18-22.

Hopkins et al., "Safety, Plasma Pharmacokinetics, and Anti-Viral Activity of SCY-635 in Adult Patients with Chronic Hepatitis C virus Infection," *Journal of Hepatology*, 2009, vol. 50(Suppl. 1):S36 & 44th Annual meeting of the European Association for the Study of the Liver, Copenhagen, Denmark, Apr. 22-26, 2009.

Sakamoto et al., "Specific Inhibition of Hepatitis C Virus Replication by Cyclosporin A," *Gastroenterology*, 2004, vol. 126(4), p. A-764 (Abstract T1674).

SCYNEXIS Inc. Press Release, SCYNEXIS' SCY-635 Demonstrates Clinically Relevant Single-agent Results in a Phase 1b Study in Adults with HCV (Results presented in an oral presentation at EASL; Phase 2 studies to be initiated in 2H09), Research Triangle Park, NC, USA, Apr. 24, 2009.

Carry, Jean-Christophe et al., "Semisynthetic Di- and Tri-Functionalized Non-Immunosuppresive Cyclosporin A Derivatives as Potential Anti-HIV 1 Drugs," SYNLETT 2004, (Feb. 2, 2004), No. 2, pp. 316-320, XP00257812 ISSN: 0936-5214.

International Searching Authority, "Notification of Transmittal of the International Search Report and the Written Opinion of the International Searching Authority, or the Declaration, for PCT/EP2009/068017" (May 6, 2010), pp. 1-12.

The State Intellectual Property Office of the People's Republic of China, The First Office Action (For the National Phase of the PCT Application) in related application CN 200980156322.2, issued Jan. 22, 2013.

* cited by examiner

MACROCYCLES

CROSS REFERENCE TO RELATED APPLICATIONS

The present application claims the benefit of priority of U.S. Provisional Application No. 61/142,068, filed Dec. 31, 2008, the content of which is hereby incorporated by reference in its entirety.

FIELD OF THE INVENTION

Disclosed herein are novel compounds, compositions comprising them, processes for their preparation, intermediates in their synthesis, and their use as therapeutics, for example as antiviral agents.

BACKGROUND OF THE INVENTION

Cyclosporine A is well known for its immunosuppressive activity and a range of therapeutic uses, including antifungal, anti-parasitic, and anti-inflammatory as well as anti-HIV activity. Cyclosporine A and certain derivatives have been reported as having anti-HCV activity, see Watashi et al., *Hepatology*, 2003, 38: 1282-1288, Nakagawa et al., *Biochem. Biophys. Res. Commun.* 2004, 313: 42-7, and Shimotohno and K. Watashi, 2004, *American Transplant Congress*, Abstract No. 648 (*American Journal of Transplantation* 2004, Volume 4, Issue s8, Pages 1-653).

Cyclosporine A (cyclosporine) derivatives modified in the 4-position to introduce hydroxyl are known in the literature. For example, [4'-Hydroxy-N-methylleucine]$^4$cyclosporine A is disclosed in European Patent No. 484,281, and is stated to be active against HIV-1 replication. 3-Ether/thioether-[4'-hydroxy-N-methylleucine]$^4$cyclosporine A derivatives are described in U.S. Pat. Nos. 5,948,755, 5,994,299, 5,948,884, and 6,583,265; and International Patent Publication Nos. WO2006/039668 and WO07/041631. Certain cyclosporine A derivatives with (4-acetoxy-N-methylleucine) in the 4-position and (3'-acetoxy-N-methyl-Bmt) in the 1-position are described in International Patent Publication No. WO2006/039668, U.S. Pat. No. 7,196,161 B2 and Carry et al., *Synlett* (2004), No. 2, pages 316-320. Cyclosporine A derivatives with (4-acetoxy-N-methylleucine) in the 4-position are described in International Patent Publication No. WO 98/49193, U.S. Pat. No. 5,977,067 and Carry et al., *Synlett* (2004), No. 2, pages 316-320. These compounds are not disclosed as having biological activity.

SUMMARY OF THE INVENTION

In one aspect, provided herein are compounds of general formula (I):

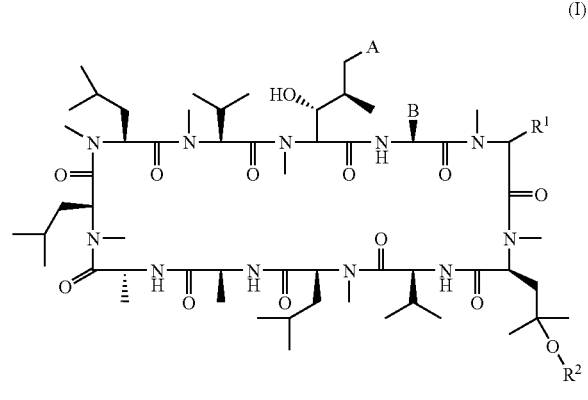

(I)

wherein:

A is (E) —CH═CHR or —CH$_2$CH$_2$R, wherein R represents methyl, —CH$_2$SH, —CH$_2$(thioalkyl), —CH$_2$(carboxyl), —CH$_2$alkoxycarbonyl, carboxyl or alkoxycarbonyl;

B represents ethyl, 1-hydroxyethyl, isopropyl or n-propyl;

R$^1$ represents hydrogen, lower alkyl, allyl or —XR$^{10}$;

R$^2$ represents —C(═O)R$^{21}$;

X represents —S(═O)$_n$— or oxygen, where n is zero, one or two;

R$^{10}$ represents:

straight- or branched-chain alkyl having from one to six carbon atoms, optionally substituted by one or more groups R$^3$ which may be the same or different;

straight- or branched-chain alkenyl having from two to six carbon atoms optionally substituted by one or more substituents which may be the same or different selected from the group consisting of halogen, hydroxy, amino, N-monoalkylamino and N,N-dialkylamino;

straight- or branched-chain alkynyl having from two to six carbon atoms, optionally substituted by one or more substituents which may be the same or different selected from the group consisting of halogen, hydroxy, amino, N-monoalkylamino and N,N-dialkylamino;

cycloalkyl containing from three to six carbon atoms optionally substituted by one or more substituents which may be the same or different selected from the group consisting of halogen, hydroxy, amino, N-monoalkylamino and N,N-dialkylamino;

or straight- or branched-chain alkoxycarbonyl having from two to six carbon atoms;

R$^3$ is selected from the group consisting of halogen; hydroxy; alkoxy; carboxyl; alkoxycarbonyl; —NR$^4$R$^5$, —NR$^6$(CH$_2$)$_m$NR$^4$R$^5$; phenyl optionally substituted by one or more substituents which may be the same or different selected from the group consisting of halogen, alkyl, alkoxy, haloalkyl, cyano, amino, N-alkylamino and N,N-dialkylamino; and a heterocyclic ring which may be saturated or unsaturated containing five or six ring atoms and from one to three heteroatoms which may be the same or different selected from the group consisting of nitrogen, sulfur and oxygen, wherein said heterocyclic ring is attached to alkyl via a ring carbon atom;

R$^4$ and R$^5$, which may be the same or different, each represent:

hydrogen;

straight- or branched-chain alkyl having from one to six carbon atoms, optionally substituted by one or more groups R$^7$ which may be the same or different;

straight- or branched-chain alkenyl or alkynyl having from two to four carbon atoms;

cycloalkyl containing from three to six carbon atoms optionally substituted by straight- or branched-chain alkyl containing from one to six carbon atoms;

phenyl optionally substituted by from one to five substituents which may be the same or different selected from the group consisting of halogen, alkoxy, cyano, alkoxycarbonyl, amino, alkylamino and dialkylamino;

a heterocyclic ring which may be saturated or unsaturated containing five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four substituents which may be the same or different selected from the group consisting of alkyl, phenyl and benzyl;

$R^6$ represents hydrogen or straight- or branched-chain alkyl having from one to six carbon atoms;

$R^7$ represents halogen, hydroxy, carboxyl, alkoxycarbonyl or —$NR^8R^9$;

$R^8$ and $R^9$ which may be the same or different, each represent hydrogen or straight- or branched-chain alkyl having from one to six carbon atoms;

$R^{21}$ represents:

hydrogen, or straight- or branched-chain alkyl having from one to six carbon atoms, optionally substituted by one or more groups $R^{22}$ which may be the same or different;

straight- or branched-chain alkenyl having from two to six carbon atoms optionally substituted by one or more substituents which may be the same or different selected from the group consisting of halogen, hydroxy, carboxyl, amino, N-monoalkylamino and N,N-dialkylamino;

straight- or branched-chain alkynyl having from two to six carbon atoms, optionally substituted by one or more substituents which may be the same or different selected from the group consisting of halogen, hydroxy, carboxyl, amino, N-monoalkylamino and N,N-dialkylamino;

cycloalkyl containing from three to six carbon atoms optionally substituted by one or more substituents which may be the same or different selected from the group consisting of halogen, hydroxy, carboxyl, amino, N-monoalkylamino and N,N-dialkylamino;

—$OR^{11}$, —$SR^{11}$, —$NR^{12}R^{13}$;

aminocarbonyl, N-mono(lower alkyl)aminocarbonyl or N,N-di(lower alkyl)aminocarbonyl;

phenyl optionally substituted by one or more substituents which may be the same or different selected from the group consisting of halogen, alkyl, alkoxy, haloalkyl, cyano, nitro, amino, N-alkylamino and N,N-dialkylamino;

or a heterocyclic ring which may be saturated or unsaturated containing from four to six ring atoms and from one to three heteroatoms which may the same or different selected from nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

$R^{11}$ represents:

straight- or branched-chain alkyl having from one to six carbon atoms, optionally substituted by one or more groups $R^{23}$ which may be the same or different;

phenyl optionally substituted by one or more substituents which may be the same or different selected from the group consisting of halogen, alkyl, alkoxy, haloalkyl, cyano, nitro, amino, N-alkylamino and N,N-dialkylamino;

$R^{12}$ and $R^{13}$, which may be the same or different, each represents:

hydrogen;

straight- or branched-chain alkyl having from one to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;

straight- or branched-chain alkenyl having from two to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;

straight- or branched-chain alkynyl having from two to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;

phenyl optionally substituted by one or more substituents which may be the same or different selected from the group consisting of halogen, alkyl, alkoxy, haloalkyl, cyano, nitro, amino, N-alkylamino and N,N-dialkylamino;

benzyl, wherein the phenyl ring is optionally substituted by one or more substituents which may be the same or different selected from the group consisting of halogen, alkyl, alkoxy, haloalkyl, cyano, nitro, amino, N-alkylamino and N,N-dialkylamino;

or $R^{12}$ and $R^{13}$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four substituents which may be the same or different selected from the group consisting of alkyl, phenyl and benzyl;

$R^{22}$ and $R^{23}$, which may be the same or different, each represents:

halogen; hydroxy; alkoxy; carboxyl; alkoxycarbonyl; amino; N-monoalkylamino; N,N-dialkylamino; —$S(=O)_p$alkyl; —$S(=O)_p$aryl; cycloalkyl containing from three to six carbon atoms optionally substituted by one or more substituents which may be the same or different selected from the group consisting of halogen, hydroxy, amino, N-monoalkylamino and N,N-dialkylamino; phenyl optionally substituted by one or more substituents which may be the same or different selected from the group consisting of halogen, alkyl, alkoxy, haloalkyl, cyano, amino, N-alkylamino and N,N-dialkylamino; or a heterocyclic ring which may be saturated or unsaturated containing four, five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkyl, alkoxy, haloalkyl, cyano, amino, N-alkylamino and N,N-dialkylamino;

p is zero, one or two;

m is an integer from two to four;

or a pharmaceutically acceptable salt or solvate thereof.

In certain cases the substituents A, B, $R^1$ and $R^2$ may contribute to optical and/or stereoisomerism. All such forms are embraced by the present invention.

In another aspect, provided are compositions comprising a compound of formula (I) along with a pharmaceutically acceptable excipient, carrier or diluent.

In another aspect, provided are pharmaceutically acceptable salts of a compound of formula (I). Examples of pharmaceutically acceptable salts include salts with alkali metals, e.g., sodium, potassium or lithium, or with alkaline-earth metals, e.g., magnesium or calcium, the ammonium salt or the salts of nitrogenous bases, e.g., ethanolamine, diethanolamine, trimethylamine, triethylamine, methylamine, propylamine, diisopropylamine, N,N-dimethylethanolamine, benzylamine, dicyclohexylamine, N-benzylphenethylamine, N,N'-dibenzylethylenediamine, diphenylenediamine, benzhydrylamine, quinine, choline, arginine, lysine, leucine or dibenzylamine.

In another aspect, provided herein are methods of using a compound of formula (I), or a composition comprising a compound of formula (I), to treat or prevent an infection, a neurodegenerative disease, ischemialreperfusion damage, an inflammatory disease or an autoimmune disease. The methods generally comprise administering to a subject having the condition or disease an amount of the compound or composition effective to treat or prevent the disease or condition. Exemplary infections include HCV or HIV infection and others described in detail herein.

In another aspect, provided herein is a compound of formula (I), or a composition comprising a compound of formula (I), for use in therapy.

In another aspect, provided herein is a compound of formula (I), or a composition comprising a compound of formula (I), for use in treatment or prevention of an infection, a neurodegenerative disease, ischemia/reperfusion damage, an inflammatory disease or an autoimmune disease.

In another aspect, provided herein is a compound of formula (I), or a composition comprising a compound of formula (I), in the manufacture of a medicament.

In another aspect, provided is a compound of formula (I), or a composition comprising a compound of formula (I), for use in the manufacture of a medicament for treatment or prevention of an infection, a neurodegenerative disease, ischemia/reperfusion damage, an inflammatory disease or an autoimmune disease.

DETAILED DESCRIPTION

Definitions

When referring to the compounds and complexes disclosed herein, the following terms have the following meanings unless indicated otherwise.

"Cyclosporine" refers to any cyclosporine compound known to those of skill in the art, or a derivative thereof. See, e.g., Ruegger et al., 1976, *Helv. Chim. Acta.* 59: 1075-92; Borel et al., 1977, *Immunology* 32: 1017-25; the contents of which are hereby incorporated by reference in their entireties. Exemplary compounds of formula (I) are cyclosporine derivatives. Unless noted otherwise, a cyclosporine described herein is a cyclosporine A, and a cyclosporine derivative described herein is a derivative of cyclosporine A.

The cyclosporine nomenclature and numbering systems used hereafter are those used by J. Kallen et al., "Cyclosporins: Recent Developments in Biosynthesis, Pharmacology and Biology, and Clinical Applications", Biotechnology, second edition, H.-J. Rehm and G. Reed, ed., 1997, p 535-591 and are shown below:

| Position | Amino acid in cyclosporine A |
|---|---|
| 1 | N-Methyl-butenyl-threonine (MeBmt) |
| 2 | [alpha]-aminobutyric acid (Abu) |
| 3 | Sarcosine (Sar) |
| 4 | N-Methyl-leucine (MeLeu) |
| 5 | Valine (Val) |
| 6 | N-Methyl-leucine (MeLeu) |
| 7 | Alanine (Ala) |
| 8 | (D)-Alanine ((D)-Ala) |
| 9 | N-Methyl-leucine (Me-Leu) |

-continued

| Position | Amino acid in cyclosporine A |
|---|---|
| 10 | N-Methyl-leucine (MeLeu) |
| 11 | N-Methylvaline (MeVal) |

This corresponds to the saturated ring carbon atoms in the compounds of formula (I) as shown below:

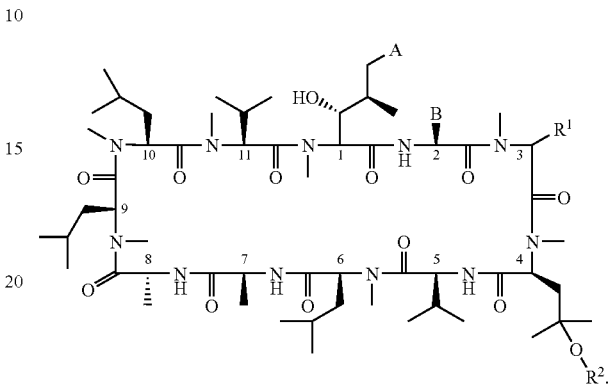

"Alkyl" refers to monovalent saturated aliphatic hydrocarbyl groups particularly having up to 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl, and the like.

"Alkylene" refers to divalent saturated aliphatic hydrocarbyl groups particularly having up to 11 carbon atoms and more particularly 1 to 6 carbon atoms which can be straight-chained or branched. This term is exemplified by groups such as methylene ($-CH_2-$), ethylene ($-CH_2CH_2-$), the propylene isomers (e.g., $-CH_2CH_2CH_2-$ and $-CH(CH_3)CH_2-$), and the like.

"Alkenyl" refers to monovalent olefinically unsaturated hydrocarbyl groups, in one embodiment, having up to 11 carbon atoms, in other embodiment, from 2 to 8 carbon atoms, and in another embodiment, from 2 to 6 carbon atoms, which can be straight-chained or branched and having at least 1 or from 1 to 2 sites of olefinic unsaturation. In some embodiments, alkenyl groups include ethenyl ($-CH=CH_2$), n-propenyl ($-CH_2CH=CH_2$), isopropenyl ($-C(CH_3)=CH_2$), vinyl and substituted vinyl, and the like.

"Alkenylene" refers to divalent olefinically unsaturated hydrocarbyl groups particularly having up to 11 carbon atoms and more particularly 2 to 6 carbon atoms which can be straight-chained or branched and having at least 1 and particularly from 1 to 2 sites of olefinic unsaturation. This term is exemplified by groups such as ethenylene ($-CH=CH-$), the propenylene isomers (e.g., $-CH=CHCH_2-$ and $-C(CH_3)=CH-$ and $-CH=C(CH_3)-$), and the like.

"Alkynyl" refers to acetylenically unsaturated hydrocarbyl groups particularly having up to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl ($-C≡CH$), propargyl ($-CH_2C≡CH$), and the like.

"Alkoxy" refers to the group -OR where R is alkyl. The alkyl group has up to 11 carbon atoms, more particularly as a lower alkyl, from 1 to 8 carbon atoms and still more particularly, from 1 to 6 carbon atoms. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"N-Alkylamino" refers to the group H—NR'—, wherein R' is selected from hydrogen and alkyl. The alkyl group has up to 11 carbon atoms, more particularly as a lower alkyl, from 1 to 8 carbon atoms and still more particularly, from 1 to 6 carbon atoms.

"Alkoxycarbonyl" refers to a radical —C(=O)-alkoxy where alkoxy is as defined herein.

"Allyl" refers to the radical $H_2C$=C(H)—C($H_2$)—.

"Amino" refers to the radical —$NH_2$.

"Aryl" refers to an optionally substituted aromatic hydrocarbon radical, for example phenyl.

"Arylamino" refers to the group aryl-NR'—, wherein R' is selected from hydrogen, aryl and heteroaryl.

"Bmt" refers to 2(S)-amino-3(R)-hydroxy-4(R)-methyl-6 (E)-octenoic acid.

"Cpd" means compound.

"Carboxyl" refers to the radical —C(=O)OH.

"N,N-Dialkylamino" means a radical —NRR' where R and R' independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Halogen" or "halo" refers to chloro, bromo, fluoro or iodo.

"Heteroaryl" refers to an optionally substituted saturated or unsaturated heterocyclic radical. Generally the heterocyclic ring contains from 4 to 7 ring atoms, e.g., 5 or 6 ring atoms. Examples of heteroaryl include thienyl, furyl, pyrrolyl, oxazinyl, thiazinyl, pyrazinyl, pyrimidinyl, pyridazinyl, thiazolyl, oxazolyl, imidazolyl, morpholinyl, pyrazolyl, tetrahydorfuryl oxadiazolyl, thiadiazolyl and isoxazolyl.

"Hydroxy" refers to the radical —OH.

"Thioalkyl" refers to the group —SR where R is alkyl. The alkyl group has up to 11 carbon atoms, more particularly as a lower alkyl, from 1 to 8 carbon atoms and still more particularly, from 1 to 6 carbon atoms. Examples include, but are not limited to, methylthio, ethylthio, propylthio, butylthio, and the like.

"Pharmaceutically acceptable salt" refers to any salt of a compound disclosed herein which retains its biological properties and which is not toxic or otherwise undesirable for pharmaceutical use. Such salts may be derived from a variety of organic and inorganic counter-ions well known in the art. Such salts include: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Salts further include, by way of example only, sodium, potassium, calcium, magnesium, ammonium, tetraalkylammonium, and the like, and when the compound contains a basic functionality, salts of non-toxic organic or inorganic acids, such as hydrohalides, e.g., hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl) benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalene-sulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations, and the like.

"Solvate" refers to a compound disclosed herein or a salt thereof that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Calm and Prelog (Calm et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds disclosed herein may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

In certain embodiments, the compounds disclosed herein are "stereochemically pure". A stereochemically pure compound has a level of stereochemical purity that would be recognized as "pure" by those of skill in the art. Of course, this level of purity will be less than 100%. In certain embodiments, "stereochemically pure" designates a compound that is substantially free of alternate isomers. In particular embodiments, the compound is 85%, 90%, 91%, 92%, 93%, 94%, 95%, 96%, 97%, 98%, 99%, 99.5% or 99.9% free of other isomers.

"Sarcosine" or "Sar" refers to the amino acid residue known to those of skill in the art having the structure —N(Me)CH$_2$C(=O)—. Those of skill in the art might recognize sarcosine as N-methyl glycine.

As used herein, the terms "subject" and "patient" are used interchangeably herein. The terms "subject" and "subjects" refer to an animal, in some embodiments, a mammal including a non-primate (e.g., a cow, pig, horse, cat, dog, rat, and mouse) and a primate (e.g., a monkey such as a cynomolgous monkey, a chimpanzee and a human), and a human. In another embodiment, the subject is a farm animal (e.g., a horse, a cow, a pig, etc.) or a pet (e.g., a dog or a cat). In one embodiment, the subject is a human.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound disclosed herein. In certain other embodiments, the term "therapeutic agent" does not refer to a compound disclosed herein. In one embodiment, a therapeutic agent is an agent that is known to be useful for, or has been or is currently being used for the treatment, management, prevention, or amelioration of a disorder or one or more symptoms thereof.

"Therapeutically effective amount" means an amount of a compound or complex or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"THF" means tetrahydrofuran.

"Treating" or "treatment" of any disease or disorder refers, in one embodiment, to ameliorating a disease or disorder that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound disclosed herein. In certain other embodiments, the term "prophylactic agent" does not refer a compound disclosed herein. In one embodiment, a prophylactic agent is an agent which is known to be useful for, or has been or is currently being used to prevent or impede the onset, development, progression and/or severity of a disorder.

As used herein, the terms "prevent", "preventing" and "prevention" refer to the prevention of the recurrence, onset, or development of one or more symptoms of a disorder in a subject resulting from the administration of a therapy (e.g., a prophylactic or therapeutic agent), or the administration of a combination of therapies (e.g., a combination of prophylactic or therapeutic agents).

As used herein, the phrase "prophylactically effective amount" refers to the amount of a therapy (e.g., prophylactic agent) which is sufficient to result in the prevention of the development, recurrence or onset of one or more symptoms associated with a disorder, or to enhance or improve the prophylactic effect(s) of another therapy (e.g., another prophylactic agent).

The term "label" refers to a display of written, printed or graphic matter upon the immediate container of an article, for example, the written material displayed on a vial containing a pharmaceutically active agent.

The term "labeling" refers to all labels and other written, printed or graphic matter upon any article or any of its containers or wrappers or accompanying such article, for example, a package insert or instructional videotapes or DVDs accompanying or associated with a container of a pharmaceutically active agent.

Compounds

In one embodiment there are provided compounds of formula (I) above wherein:

A is (E) —CH=CHR or —CH$_2$CH$_2$R, wherein R represents methyl, —CH$_2$SH, —CH$_2$(thioalkyl), —CH$_2$(carboxyl) or —CH$_2$alkoxycarbonyl;

B represents ethyl, 1-hydroxyethyl, isopropyl or n-propyl;

$R^1$ represents hydrogen, lower alkyl, allyl or —XR$^{10}$;

$R^2$ represents —C(=O)R$^{21}$;

X represents —S(=O)$_n$— or oxygen, where n is zero, one or two;

R represents:
straight- or branched-chain alkyl having from one to six carbon atoms, optionally substituted by one or more groups $R^3$ which may be the same or different;
straight- or branched-chain alkenyl having from two to six carbon atoms optionally substituted by one or more substituents which may be the same or different selected from the group consisting of halogen, hydroxy, amino, N-monoalkylamino and N,N-dialkylamino;
straight- or branched-chain alkynyl having from two to six carbon atoms, optionally substituted by one or more substituents which may be the same or different selected from the group consisting of halogen, hydroxy, amino, N-monoalkylamino and N,N-dialkylamino;
cycloalkyl containing from three to six carbon atoms optionally substituted by one or more substituents which may be the same or different selected from the group consisting of halogen, hydroxy, amino, N-monoalkylamino and N,N-dialkylamino;
or straight- or branched-chain alkoxycarbonyl having from two to six carbon atoms;

$R^3$ is selected from the group consisting of halogen; hydroxy; alkoxy; carboxyl; alkoxycarbonyl; —NR$^4$R$^5$, —NR$^6$(CH$_2$)$_m$NR$^4$R$^5$; phenyl optionally substituted by one or more substituents which may be the same or different selected from the group consisting of halogen, alkyl, alkoxy, haloalkyl, cyano, amino, N-alkylamino and N,N-dialkylamino; and a heterocyclic ring which may be saturated or unsaturated containing five or six ring atoms and from one to three heteroatoms which may be the same or different selected from the group consisting of nitrogen, sulfur and oxygen, wherein said heterocyclic ring is attached to alkyl via a ring carbon atom;

$R^4$ and $R^5$, which may be the same or different, each represent:

p hydrogen;

straight- or branched-chain alkyl having from one to six carbon atoms, optionally substituted by one or more groups $R^7$ which may be the same or different;

straight- or branched-chain alkenyl or alkynyl having from two to four carbon atoms;

cycloalkyl containing from three to six carbon atoms optionally substituted by straight- or branched-chain alkyl containing from one to six carbon atoms;

phenyl optionally substituted by from one to five substituents which may be the same or different selected from the group consisting of halogen, alkoxy, cyano, alkoxycarbonyl, amino, alkylamino and dialkylamino;

a heterocyclic ring which may be saturated or unsaturated containing five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four substituents which may be the same or different selected from the group consisting of alkyl, phenyl and benzyl;

$R^6$ represents hydrogen or straight- or branched-chain alkyl having from one to six carbon atoms;

$R^7$ represents halogen, hydroxy, carboxyl, alkoxycarbonyl or —$NR^8R^9$;

$R^8$ and $R^9$ which may be the same or different, each represent hydrogen or straight- or branched-chain alkyl having from one to six carbon atoms;

$R^{21}$ represents:

hydrogen, or straight- or branched-chain alkyl having from one to six carbon atoms, optionally substituted by one or more groups $R^{22}$ which may be the same or different;

straight- or branched-chain alkenyl having from two to six carbon atoms optionally substituted by one or more substituents which may be the same or different selected from the group consisting of halogen, hydroxy, carboxyl, amino, N-monoalkylamino and N,N-dialkylamino;

straight- or branched-chain alkynyl having from two to six carbon atoms, optionally substituted by one or more substituents which may be the same or different selected from the group consisting of halogen, hydroxy, carboxyl, amino, N-monoalkylamino and N,N-dialkylamino;

cycloalkyl containing from three to six carbon atoms optionally substituted by one or more substituents which may be the same or different selected from the group consisting of halogen, hydroxy, carboxyl, amino, N-monoalkylamino and N,N-dialkylamino; aminocarbonyl, N-mono(lower alkyl)aminocarbonyl or N,N-di(lower alkyl)aminocarbonyl;

phenyl optionally substituted by one or more substituents which may be the same or different selected from the group consisting of halogen, alkyl, alkoxy, haloalkyl, cyano, amino, N-alkylamino and N,N-dialkylamino;

or a heterocyclic ring which may be saturated or unsaturated containing from four to six ring atoms and from one to three heteroatoms which may the same or different selected from nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

$R^{22}$ represents:

halogen; hydroxy; alkoxy; carboxyl; alkoxycarbonyl; amino; N-monoalkylamino; N,N-dialkylamino; —S(=O)$_p$alkyl; —S(=O)$_p$aryl; cycloalkyl containing from three to six carbon atoms optionally substituted by one or more substituents which may be the same or different selected from the group consisting of halogen, hydroxy, amino, N-monoalkylamino and N,N-dialkylamino; phenyl optionally substituted by one or more substituents which may be the same or different selected from the group consisting of halogen, alkyl, alkoxy, haloalkyl, cyano, amino, N-alkylamino and N,N-dialkylamino; or a heterocyclic ring which may be saturated or unsaturated containing four, five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkyl, alkoxy, haloalkyl, cyano, amino, N-alkylamino and N,N-dialkylamino;

p is zero, one or two;

m is an integer from two to four;

or a pharmaceutically acceptable salt or solvate thereof.

In certain embodiments, A represents (E)—CH=CHR. In further embodiments, A represents —CH$_2$CH$_2$R. In one embodiment, A represents (E)—CH=CHR.

In one embodiment A is (E)—CH=CHR or —CH$_2$CH$_2$R, wherein R represents methyl, —CH$_2$SH, —CH$_2$(thioalkyl), —CH$_2$(carboxyl) or —CH$_2$(alkoxycarbonyl).

In one embodiment, R represents methyl.

In one embodiment, B represents ethyl.

In one embodiment, $R^1$ represents hydrogen or —$XR^{10}$. In another embodiment $R^1$ represents methyl.

In certain embodiments, $R^{10}$ represents straight- or branched-chain alkyl having from one to four carbon atoms optionally substituted by a group $R^3$. In a further embodiment $R^{10}$ represents methyl or ethyl, optionally substituted by a group $R^3$. In a further embodiment $R^{10}$ represents ethyl substituted by a group $R^3$. In another embodiment, $R^{10}$ represents methyl.

In certain embodiments, $R^3$ represents —$NR^4R^5$, wherein $R^4$ and $R^5$, which may be the same or different, each represent hydrogen or straight- or branched-chain alkyl having from one to four carbon atoms. In further embodiments, $R^3$ represents —$NR^4R^5$, wherein $R^4$ and $R^5$ each represent methyl or ethyl. In a still further embodiment, $R^3$ represents —$NR^4R^5$, wherein $R^4$ and $R^5$ each represent methyl.

In some embodiments, X is oxygen or sulfur or nitrogen. In certain embodiments, X is oxygen or sulphur. In further embodiments X is oxygen. In still further embodiments, X is sulfur.

In certain embodiments $R^{21}$ represents straight- or branched-chain alkyl having from one to four carbon atoms, optionally substituted by one or more groups $R^{22}$. In a further embodiment $R^{21}$ represents methyl, optionally substituted by a group $R^{22}$. In a still further embodiment $R^{21}$ represents methyl.

In a further embodiment $R^{21}$ represents:
straight- or branched-chain alkyl having from one to six carbon atoms, optionally substituted by one or more groups $R^{22}$ which may be the same or different;
straight- or branched-chain alkenyl having from three to six carbon atoms;
—$OR^{11}$, —$SR^{11}$ or —$NR^{12}R^{13}$.

In one embodiment $R^{22}$ represents alkoxy, amino, N-monoalkylamino or N,N-dialkylamino. In further embodiments $R^{22}$ represents amino, N-monoalkylamino or N,N-dialkylamino. In a still further embodiment, $R^{22}$ represents N,N-dialkylamino. In a still further embodiment, $R^{22}$ represents N,N-dimethylamino or N,N-diethylamino.

In one embodiment $R^{11}$ represents:
straight- or branched-chain alkyl having from one to six carbon atoms, optionally substituted by a group $R^{23}$;
or phenyl optionally substituted by one or more substituents which may be the same or different selected from the group consisting of halogen, alkyl, alkoxy, haloalkyl, cyano, nitro, amino, N-alkylamino and N,N-dialkylamino.

In one embodiment $R^{23}$ represents phenyl optionally substituted by one or more substituents which may be the same or different selected from the group consisting of halogen, alkyl, alkoxy, haloalkyl, cyano, amino, N-alkylamino and N,N-dialkylamino. In another embodiment $R^{23}$ represents N,N-dialkylamino, or phenyl optionally substituted by N,N-dialkylamino.

In certain embodiments $R^{12}$ and $R^{13}$, which may be the same or different, each represents:
hydrogen;
straight- or branched-chain alkyl having from one to six carbon atoms;
straight- or branched-chain alkenyl having from two to six carbon atoms;
benzyl, wherein the phenyl ring is optionally substituted by one or more substituents which may be the same or different selected from the group consisting of halogen, alkyl, alkoxy, haloalkyl, cyano, nitro, amino, N-alkylamino and N,N-dialkylamino;
or $R^{12}$ and $R^{13}$, together with the nitrogen atom to which they are attached, form a saturated heterocyclic ring containing from four to six ring atoms, which ring may optionally contain another heteroatom selected from the group consisting of nitrogen, oxygen and sulfur and may be optionally substituted by one or more groups alkyl which may be the same or different.

In another embodiment $R^{12}$ and $R^{13}$, which may be the same or different, each represents: hydrogen; straight- or branched-chain alkyl having from one to six carbon atoms; straight- or branched-chain alkenyl having from three to six carbon atoms; benzyl, wherein the phenyl ring is optionally substituted by one or two substituents which may be the same or different selected from the group consisting of halogen, alkyl, alkoxy, haloalkyl, cyano, nitro, amino, N-alkylamino and N,N-dialkylamino; or $R^{12}$ and $R^{13}$, together with the nitrogen atom to which they are attached, form a saturated heterocyclic ring containing from four to six ring atoms, which ring may optionally contain a further nitrogen atom and is optionally substituted by one or more groups alkyl which may be the same or different.

In yet another embodiment $R^{12}$ and $R^{13}$, which may be the same or different, each represents: hydrogen; straight- or branched-chain alkyl having from one to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl; straight- or branched-chain alkenyl having from three to six carbon atoms; benzyl, wherein the phenyl ring is optionally substituted by alkoxy; or $R^{12}$ and $R^{13}$, together with the nitrogen atom to which they are attached, form a saturated heterocyclic ring containing from four to six ring atoms, which ring may optionally contain a further nitrogen atom and is optionally substituted by one or more groups alkyl which may be the same or different.

In certain embodiments there are provided compounds of formula (I) in which A represents (E) —CH═CHCH$_3$; B represents ethyl; $R^1$ represents hydrogen or —$XR^{10}$; X represents oxygen or sulfur; $R^{10}$ represents alkyl (e.g., methyl); and $R^{21}$ represents straight- or branched-chain alkyl having from one to four carbon atoms, optionally substituted by one or more groups $R^{22}$. In a further embodiment $R^{21}$ represents methyl, optionally substituted by a group $R^{22}$. In a still further embodiment $R^{21}$ represents methyl.

In certain embodiments there are provided compounds of formula (I) in which A represents (E) —CH═CHCH$_3$; B represents ethyl; $R^1$ represents hydrogen or —$XR^{10}$; X represents oxygen or sulfur; $R^{10}$ represents alkyl (e.g., methyl); $R^{21}$ represents straight- or branched-chain alkyl having from one to four carbon atoms, optionally substituted by one or more groups $R^{22}$; and $R^{22}$ represents alkoxy, amino, N-monoalkylamino or N,N-dialkylamino. In further embodiments $R^{22}$ represents amino, N-monoalkylamino or N,N-dialkylamino. In a still further embodiment, $R^{22}$ represents N,N-dialkylamino. In a still further embodiment, $R^{22}$ represents N,N-dimethylamino or N,N-diethylamino.

In certain embodiments there are provided compounds of formula (I) in which A represents (E) —CH═CHCH$_3$; B represents ethyl; $R^1$ represents hydrogen or —$XR^{10}$; X represents oxygen or sulfur; $R^{10}$ represents alkyl (e.g., methyl); $R^{21}$ represents lower alkyl optionally substituted by a group $R^{22}$; and $R^{22}$ represents N,N-dialkylamino (e.g., N,N-dimethylamino or N,N-diethylamino).

In certain embodiments there are provided compounds of formula (I) in which:
A represents (E) —CH═CHCH$_3$;
B represents ethyl;
$R^1$ represents hydrogen or —$XR^{10}$;
X represents oxygen or sulfur;
$R^{10}$ represents alkyl (e.g., methyl);
$R^{21}$ represents:
straight- or branched-chain alkyl having from one to four carbon atoms optionally substituted by a group $R^{22}$;
—$OR^{11}$, —$SR^{11}$ or —$NR^{12}R^{13}$;
$R^{11}$ represents phenyl substituted by nitro; or benzyl;
$R^{12}$ and $R^{13}$, which may be the same or different, each represent:
hydrogen;
straight- or branched-chain alkyl having from one to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;
straight- or branched-chain alkenyl having from two to four carbon atoms;
or $R^{12}$ and $R^{13}$, together with the nitrogen atom to which they are attached, form a saturated heterocyclic ring containing from four to six ring atoms, which ring may optionally contain another nitrogen atom and may be optionally substituted by alkyl (e.g., methyl);
$R^{22}$ represents N,N-dialkylamino (e.g., N,N-dimethylamino); and
$R^{23}$ represents phenyl optionally substituted by alkoxy (e.g., methoxy); or $R^{23}$ represents N,N-dialkylamino (e.g., N,N-dimethylamino).

In one embodiment, the compounds of formula (I) provided herein are selected from the following:

| Cpd | Name |
| --- | --- |
| A | [(R)-methoxy-Sar]³[4'-acetoxy-N-methylleucine]⁴cyclosporine A |
| B | [(R)-methylthio-Sar]³[4'-N,N'-dimethylaminoacetoxy-N-methylleucine]⁴-cyclosporine A |
| C | [4'-N,N'-dimethylaminoacetoxy-N-methylleucine]⁴cyclosporine A |
| D | [4'-N,N'-diethylaminoacetoxy-N-methylleucine]⁴cyclosporine A |
| E | [4'-acetoxy-N-methylleucine]⁴cyclosporine A |
| F | [4'-trimethylacetoxy-N-methylleucine]⁴cyclosporine A |
| G | [4'-propionyloxy-N-methylleucine]⁴cyclosporine A |
| H | [4'-butyryloxy-N-methylleucine]⁴cyclosporine A |
| I | [4'-isobutyryloxy-N-methylleucine]⁴cyclosporine A |
| J | [4'-(trans-2-methyl-2-butenoyl)oxy-N-methylleucine]⁴cyclosporine A |
| K | [4'-hydroxy-N-methylleucine]⁴cyclosporine A p-nitrophenyl-4'-carbonate |
| L | [4'-hydroxy-N-methylleucine]⁴cyclosporine A N,N-dimethyl-4'-carbamate |
| M | [4'-hydroxy-N-methylleucine]⁴cyclosporine A N,N-diethyl-4'-carbamate |
| N | [4'-hydroxy-N-methylleucine]⁴cyclosporine A N-methyl-4'-carbamate |
| O | [4'-hydroxy-N-methylleucine]⁴cyclosporine A N-ethyl-4'-carbamate |
| P | [4'-hydroxy-N-methylleucine]⁴cyclosporine A N-allyl-4'-carbamate |
| Q | [4'-hydroxy-N-methylleucine]⁴cyclosporine A N-(n-butyl)-4'-carbamate |
| R | [4'-hydroxy-N-methylleucine]⁴cyclosporine A N-(n-hexyl)-4'-carbamate |
| S | [4'-hydroxy-N-methylleucine]⁴cyclosporine A N-benzyl-4'-carbamate |
| T | [4'-hydroxy-N-methylleucine]⁴cyclosporine A N-(p-methoxybenzyl)-4'-carbamate |
| U | [4'-hydroxy-N-methylleucine]⁴cyclosporine A azetidine-4'-carbamate |
| V | [4'-hydroxy-N-methylleucine]⁴cyclosporine A pyrrolidine-4'-carbamate |
| W | [4'-hydroxy-N-methylleucine]⁴cyclosporine A piperidine-4'-carbamate |
| X | [4'-hydroxy-N-methylleucine]⁴cyclosporine A S-benzyl-4'-thiocarbonate |
| Y | [4'-hydroxy-N-methylleucine]⁴cyclosporine A 4-methyl-1-piperazine-4'-carbamate |
| Z | [4'-hydroxy-N-methylleucine]⁴cyclosporine A N,N-dimethylethylenediamine-4'-carbamate. |

The letters A to Z are used to identify the above compounds hereafter.

The compounds A to J described above are named as derivatives of Cyclosporin A as the parent structure and the compounds K to Z are named as carbonate and carbamate derivatives. It will be understood that these compounds can be named according to an alternative nomenclature using a different parent structure. For example, compound E, named [4'-acetoxy-N-methylleucine]⁴cyclosporine A, can also be named [4'-hydroxy-N-methylleucine]⁴cyclosporine A 4'-acetate, and is a compound of the following formula:

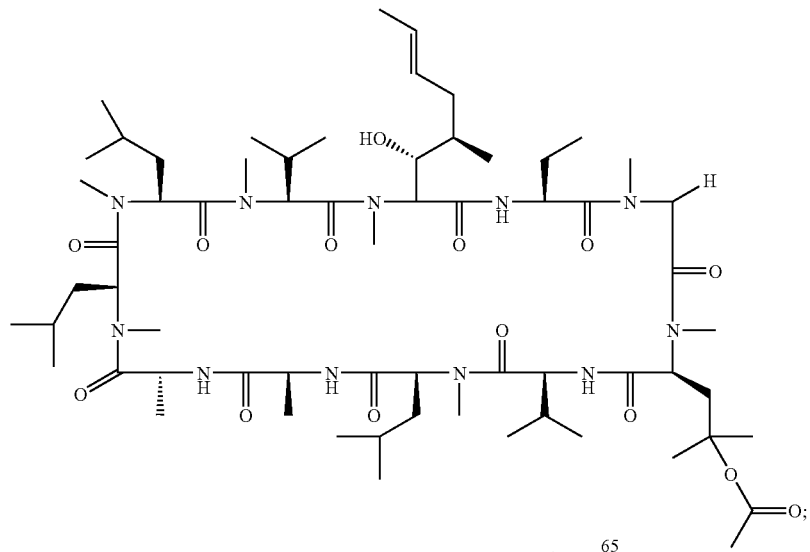 [SMILES: C/C=C/C[C@@H](C)[C@@H](O)C1C(=O)N[C@H](CC)C(=O)N(C)CC(=O)N(C)[C@@H](CC(C)(C)OC(C)=O)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

and compound L, named [4'-hydroxy-N-methylleucine]⁴cyclosporine A N,N-dimethyl-4'-carbamate, can also be named [4'-(N,N-dimethylaminocarbonyl)oxy-N-methylleucine]⁴ cyclosporine A, and is a compound of the following formula:

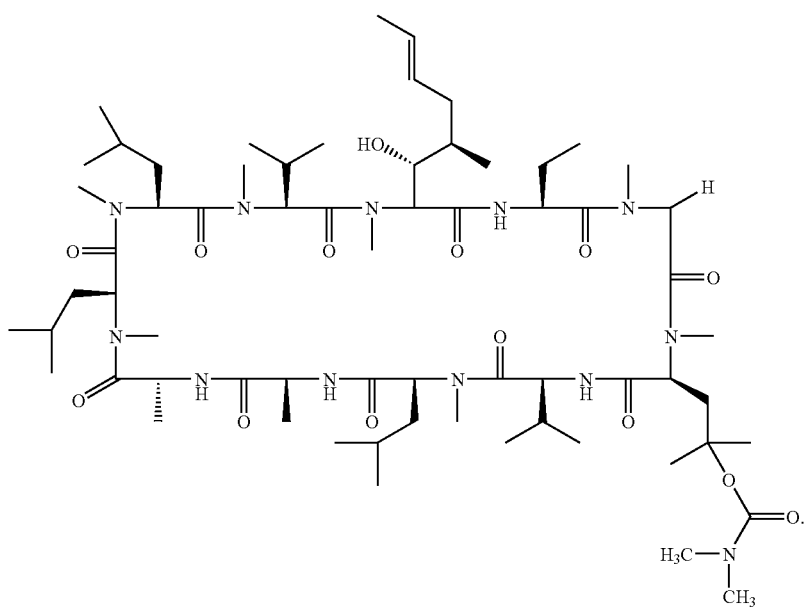 [SMILES: C/C=C/C[C@@H](C)[C@@H](O)C1C(=O)N[C@H](CC)C(=O)N(C)CC(=O)N(C)[C@@H](CC(C)(C)OC(=O)N(C)C)C(=O)N[C@H](C(C)C)C(=O)N(C)[C@H](CC(C)C)C(=O)N[C@H](C)C(=O)N[C@@H](C)C(=O)N(C)[C@H](CC(C)C)C(=O)N(C)[C@H](CC(C)C)C(=O)N(C)[C@H](C(C)C)C(=O)N1C]

The compounds of formula (I) can be prepared, isolated or obtained by any method apparent to those of skill in the art. Exemplary methods of preparation are described in detail in the examples below.

According to a feature of the present invention, compounds of formula (I) may be prepared by the deprotection of a compound of formula (II):

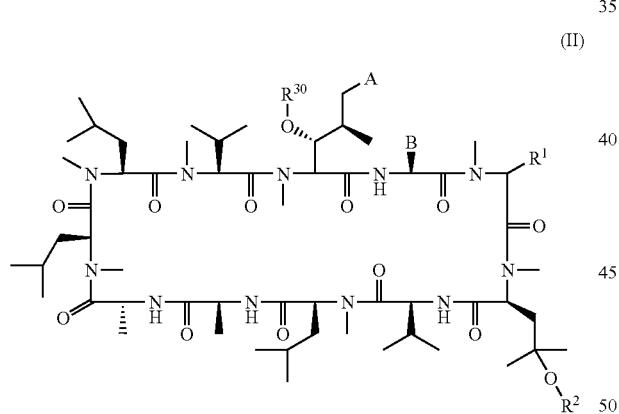

(II)

wherein $R^{30}$ represents a protecting group, to replace the protecting group with hydrogen. The protecting group may be any group that can be selectively removed, for example an acyl protecting group (e.g., acetyl, trichloroacetyl) or benzoyl group. The reaction takes place under conditions which allow removal of the protecting group with minimum effect on other groups. For example, where the protecting group is acetyl, the protecting group may be removed by reaction with a metal alkoxide such as sodium methoxide. When $R^2$ and $R^{30}$ each represent acyl then $R^{30}$ can be replaced with hydrogen without affecting $R^2$. Products may be isolated directly by crystallization, or following chromatographic procedures using silica gel or reverse-phase media.

In certain embodiments, provided herein are compounds of formula (II) wherein when $R^2$ and $R^{30}$ simultaneously represent acetyl, then $R^1$ is other than hydrogen, thiomethyl, methoxy, acetoxy or ethylene-(2,2,-diethylamino).

Compounds of formula (II) above may be prepared by reacting a compound of formula (III):

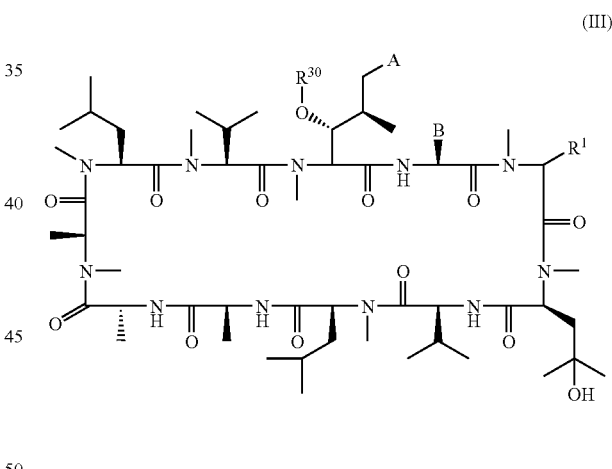

(III)

with an anhydride of formula $(R^{21}CO)_2O$ in the presence of base (e.g., pyridine) and a nucleophilic catalyst such as N,N-dimethylaminopyridine in a solvent such as dichloromethane at a temperature between about 0° C. and about 25° C. Alternatively, a compound of formula (III) may be reacted with an acyl halide ($R^{21}COCl$) in the presence of a base, such as triethylamine in a solvent, such as dichloromethane at a temperature between about 0° C. and about 25° C. Other solvents for either acylation method include toluene, tetrahydrofuran, ethyl acetate, and methyl-t-butyl ether. In certain embodiments, provided herein are compounds of formula (III).

Compounds of formula (III) above in which $R^{30}$ represents a protecting group (e.g., acetyl, trichloroacetyl) or benzoyl group can be prepared by the deprotection of compound of formula (IV):

(IV)

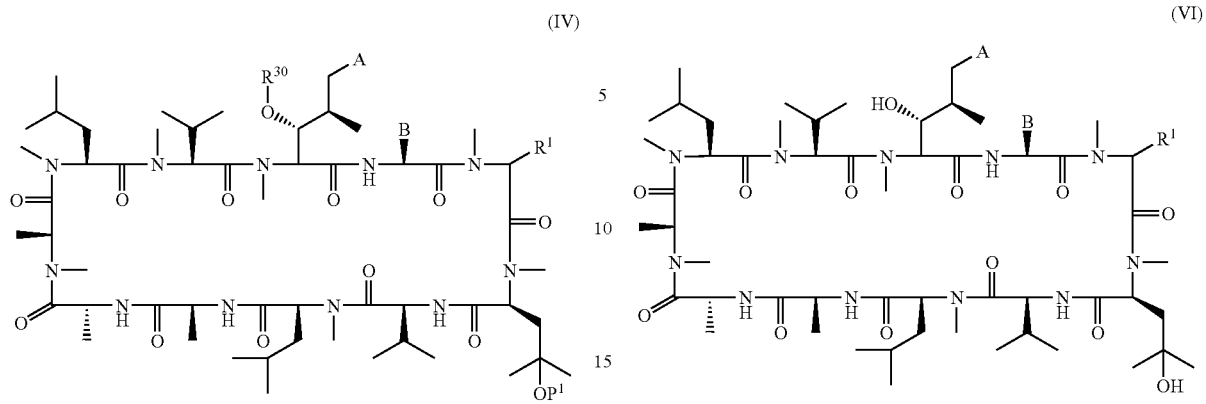

wherein P[1] represents a protecting group, for example a silyl group (e.g., trimethylsilyl, triethylsilyl triisopropylsilyl or tert-butyldimethylsilyl) with an tetraalkylammonium halide, e.g., tetrabutylammonium fluoride, or under acidic conditions. In certain embodiments, provided herein are compounds of formula (IV).

Compounds of formula (IV) above can be prepared by treating a compound of formula (V):

(V)

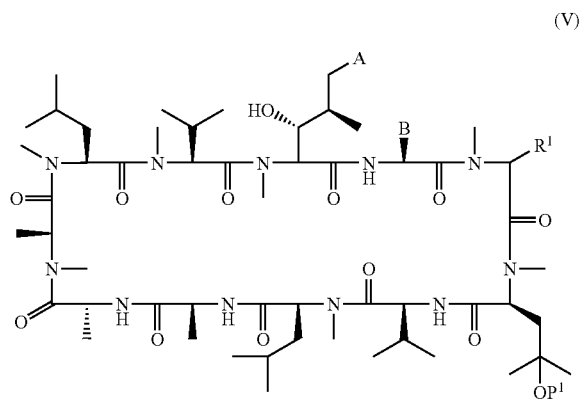

in which P[1] represents a protecting group, for example a silyl group (e.g., trimethylsilyl, triisopropylsilyl or tert-butyldimethylsilyl) with an anhydride of formula $(R^{21}CO)_2O$ in the presence of base (e.g., pyridine) and a nucleophilic catalyst such as N,N-dimethylaminopyridine in a solvent such as dichloromethane at a temperature between about 0° C. and about 25° C. Alternatively, a compound of formula (V) may be reacted with an acyl halide ($R^{21}COCl$) in the presence of a base, such as triethylamine in a solvent, such as dichloromethane at a temperature between about 0° C. and about 25° C. Other solvents for either acylation method include toluene, tetrahydrofuran, ethyl acetate, and methyl-t-butyl ether. In certain embodiments, provided herein are compounds of formula (V).

Compound of formula (V) above can be prepared by reaction of a compound of formula (VI):

(VI)

with a silyl chloride (e.g., trimethylsilyl chloride) or silyl triflate (e.g., triisopropylsilyl triflate or tert-butyldimethylsilyl triflate) in the presence of base (e.g., pyridine, 2,6-lutidine, or triethylamine) and a nucleophilic catalyst such as N,N-dimethylaminopyridine in a solvent such as dichloromethane at a temperature between about 0° C. and about 25° C. This reaction generally occurs with a high level of regioselectivity.

According to a further feature of the present invention, compounds of formula (I) can be prepared by reaction of a compound of formula (VI) above with an anhydride of formula $(R^{21} CO)_2O$ in the presence a metal catalyst. Examples of metal catalyst include a bismuth (III) compound, for example bismuth(III) trifluoromethanesulfonate; a scandium (III) compound, for example scandium triflate; an indium (III) compound, for example indium triflate; a silyl compound, for example trimethylsilyl triflate; an organotin catalysts (generally under mild conditions mild for selective acylation reactions); a zinc (II) halide, for example zinc chloride. The reaction is preferably performed using a bismuth (III) compound, such as bismuth (III) trifluoromethanesulfonate. The reaction is generally performed using the anhydride of formula $(R^{21}CO)_2O$ itself as solvent, or in an aprotic solvent. Examples of solvents include dichloromethane, toluene, acetonitrile and tetrahydrofuran (THF). The reaction is generally performed at a temperature of from about −20° C. to 80° C., preferably from about 0° C. to about 25° C.

Compounds of formula (VI) can be prepared according to methods known to one of skill in the art, for example, methods described in U.S. Pat. Nos. 5,948,884, 5,994,299, and 6,583,265, and in International Patent Publication Nos. WO99/32512 and WO99/67280. The contents of these references are hereby incorporated by reference in their entireties.

According to a further feature of the present invention, compounds of general formula (I), (II), (III), (IV) or (V) in which X is sulfur may be prepared by treating the corresponding compound of general formula (I), (II), (III), (IV) or (V) in which —$XR^{10}$ is replaced by hydrogen, with a strong base to form a polyanion and subsequently treating the polyanion with a sulfur electrophile, to introduce a group —S—$R^{10}$. Examples of such sulfur electrophiles include disulfides of formula $R^{10}$—S—S—$R^{10}$ or sulfenyl halides of formula $R^{10}$—S-Hal, wherein Hal is a halogen. Typically the reactions are carried out under inert atmosphere (e.g., nitrogen or argon), at low temperatures (e.g., from about −80° C. to about −35° C.), and in inert solvents, in particular aprotic solvents such as tetrahydrofuran, dioxane, t-butylmethyl ether, and diethyl ether. Examples of effective bases include lithium diisopropylamide (LDA), LDA/n-butyllithium, sodium amide/ammonia, and lithium N,N-trimethylsilylamine /cesium chloride. After addition of the sulphur electrophile, the temperature is gradually increased to ambient conditions prior to workup.

According to a further feature of the present invention, compounds of the general formula (I), (II), (III), (IV) or (V) in which X is oxygen can be prepared by treating the corresponding compound of formula (I), (II) (III), (IV) or (V) in which X is sulfur with either 1) an excess of an appropriate alcohol of formula Ar-(alkylene)-OH in a suitable solvent, or 2) mercury acetate in acetic acid, followed by addition of an excess of an alcohol of formula $R^{10}$—OH. The reaction is generally effected by a Bronsted acid, and performed at elevated temperature (e.g., 50 to 60° C.) in the presence of an inert solvent such as tetrahydrofuran and dioxane. Examples of proton donating acids include sulfuric, hydrochloric, toluene sulfonic, and camphorsulfonic acids. In one embodiment, mercury acetate in acetic acid is used to produce substantially enantiomerically pure R isomer.

According to a further feature of the present invention compounds, of general formula (I), (II), (III), (IV) or (V) in which X is —$S(O)_n$ and n is one or two, or $R^{22}$ is —$S(=O)_p$ alkyl or 1 —$S(=O)_p$aryl and p is one or two, oxidizing the corresponding compound of formula (I), (II) (III), (IV) or (V) in which X is sulphur or $R^{22}$ is thioalkyl or thioaryl using an oxidizing agent in an inert solvent, and at temperatures from 0° C. to the refluxing temperature of the solvent. Organic sulfides can be oxidized to sulfoxides or sulfones using organic or inorganic oxidants. Among the prominent oxidants used for this conversion are hydrogen peroxide, chromic acid, nitric acid, manganese dioxide, ozone, peracids, selenium dioxide, sodium periodate, meta-chloroperoxybenzoic acid, hypervalent iodine reagents, sodium perborate, and dinitrogen tetroxide. A halogenated solvent, such as chloroform or dichloromethane, or a solvent mixture of a halogenated solvent and an alcohol is normally used. Metal catalysts such as $Sc(OTf)_3$, sodium tungstate and $VO(acac)_2$ may be used to facilitate the oxidation. Urea-hydrogen peroxide can be used to replace hydrogen peroxide. Sulfoxides can also be made through oxidation of sulfides with sodium periodate under heterogeneous conditions using phase transfer catalysts.

Compounds of formula (II) in which $R^1$ represents —$XR^{10}$ and $R^{10}$ represents a straight- or branched-chain alkyl having from one to six carbon atoms substituted by one or more groups $R^3$ which may be the same or different and $R^3$ is —$NR^4R^5$ and —$NR^6(CH_2)_mNR^4R^5$, may be prepared from the corresponding compound of formula (II) in which R represents straight- or branched-chain alkyl having from one to six carbon atoms substituted by one or more hydroxy, by performing a selective oxidation of the hydroxy, followed by reductive amination with a compound of formula $HNR^4R^5$ or $HNR^6(CH_2)_mNR^4R^5$. The selective oxidation may be performed using for example Dess-Martin periodinane, pyridinum chlorochromate, pyridinum dichromate, 2,2,6,6-Tetramethylpiperidinyloxy, tetrapropylammonium perruthenate or N-methylmorpholine N-oxide.

As discussed above, a compound disclosed herein can be in a neutral form, or in a salt form. The salt form can be any salt form known to those of skill in the art. Particularly useful salt forms are those that are coordinated with phosphate, citrate, acetate, chloride, methanesulfonate or propionate.

Where a compound disclosed herein is substituted with a basic moiety, an acid addition salt can be formed. The acid which can be used to prepare an acid addition salt includes that which produces, when combined with the free base, a pharmaceutically acceptable salt, that is, a salt whose anion is non-toxic to a subject in the pharmaceutical doses of the salt. Pharmaceutically acceptable salts within the scope of the invention are those derived from the following acids: mineral acids such as hydrochloric acid, hydrobromic acid, sulfuric acid, phosphoric acid, sulfamic acid and nitric acid; and organic acids such as acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo [2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

The corresponding acid addition salts include hydrohalides, e.g., hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo [2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

According to a further feature of the invention, acid addition salts of the compounds disclosed herein, for example, compounds of formula (I), can be prepared by reaction of the free base with the appropriate acid, by the application or adaptation of known methods. For example, the acid addition salts of the compounds of this invention can be prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of compounds disclosed herein, for example, compounds of formula (I), can be regenerated from the salts by the application or adaptation of known methods. For example, parent compounds of the compounds of formula (I) can be regenerated from their acid addition salts by treatment with an alkali, e.g., aqueous sodium bicarbonate solution or aqueous ammonia solution.

Where a compound disclosed herein, for example, a compound of formula (I), is substituted with an acid moiety, base addition salts can be formed. Pharmaceutically acceptable salts, including for example alkali and alkaline earth metal salts, within the scope of the invention are those derived from the following bases: sodium hydride, sodium hydroxide, potassium hydroxide, calcium hydroxide, magnesium hydroxide, aluminum hydroxide, lithium hydroxide, zinc hydroxide, barium hydroxide, and organic amines such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Metal salts of compounds disclosed herein, for example, compounds of formula (I), can be obtained by contacting a hydride, hydroxide, carbonate or similar reactive compound of the chosen metal in an aqueous or organic solvent with the free acid form of the compound. The aqueous solvent employed may be water or it may be a mixture of water with an organic solvent, in certain embodiments, an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds disclosed herein, for example, compounds of formula (I), can be obtained by contacting an amine in an aqueous or organic solvent with the free acid form of the compound. Suitable aqueous solvents include water and mixtures of water with alcohols such as methanol or ethanol, ethers such as tetrahydrofuran, nitriles, such as acetonitrile, or ketones such as acetone. Amino acid salts may be similarly prepared.

The base addition salts of the compounds disclosed herein, for example, compounds of formula (I), can be regenerated from the salts by the application or adaptation of known methods. For example, parent compounds of the compounds of formula (I) can be regenerated from their base addition salts by treatment with an acid, e.g., hydrochloric acid.

Pharmaceutical Compositions and Methods of Administration

The compounds of formula (I) used in the methods disclosed herein can be administered in certain embodiments using pharmaceutical compositions containing at least one compound of general formula (I), if appropriate in the salt form, either used alone or in the form of a combination with one or more compatible and pharmaceutically acceptable carriers, such as diluents or adjuvants, or with another anti-HCV agent. In clinical practice the cyclosporine compounds of the present invention may be administered by any conventional route, in particular orally, parenterally, rectally or by inhalation (e.g., in the form of aerosols). In one embodiment, the compounds disclosed herein are administered orally.

Use may be made, as solid compositions for oral administration, of tablets, pills, hard gelatin capsules, powders or granules. In these compositions, the active product according to the invention is mixed with one or more inert diluents or adjuvants, such as sucrose, lactose or starch.

These compositions can comprise substances other than diluents, for example a lubricant, such as magnesium stearate, or a coating intended for controlled release Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In one embodiment, a composition disclosed herein is a pharmaceutical composition or a single unit dosage form. Pharmaceutical compositions and single unit dosage forms of the invention comprise a prophylactically or therapeutically effective amount of one or more prophylactic or therapeutic agents (e.g., a compound of formula (I), or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in *Remington's Pharmaceutical Sciences*, $16^{th}$, $18^{th}$ and $20^{th}$ eds., Mack Publishing, Easton Pa. (1980, 1990 & 2000).

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions of the invention can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are, in certain embodiments, anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations, and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in one embodiment, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as an animal subject, in one embodiment, a mammalian subject, such as a human subject.

A pharmaceutical composition of the invention is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial, and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms of the invention will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences*, 20$^{th}$ ed., Mack Publishing, Easton Pa. (2000).

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms of the invention comprise a compound disclosed herein, or a pharmaceutically acceptable salt, solvate or hydrate thereof lie within the range of from about 0.1 mg to about 1000 mg per day, given as a single once-a-day dose in the morning or in one aspect, as divided doses throughout the day taken with food. In certain embodiments, dosage forms of the invention have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active cyclosporine.

Oral Dosage Forms

Pharmaceutical compositions disclosed herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 20$^{th}$ ed., Mack Publishing, Easton Pa. (2000).

In certain embodiments, the oral dosage forms are solid and prepared under anhydrous conditions with anhydrous ingredients, as described in detail in the sections above. However, the scope of the invention extends beyond anhydrous, solid oral dosage forms. As such, further forms are described herein.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC 581. Suitable anhydrous or low moisture excipients or additives include AVICEL PH 103 and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds of formula (I) can be administered by controlled release means or by delivery devices that are well known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, and 6,699,500, each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, 1987, *CRC Crit. Ref. Biomed. Eng.* 14: 201; Buchwald et al., 1980, *Surgery* 88: 507; Saudek et al., 1989, *N. Engl. J. Med.* 321: 574). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (Langer, 1990, *Science* 249: 1527-1533). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

Although solid, anhydrous oral dosage forms can be used, the present invention also provides parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are, in one embodiment, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical & Mucosal Dosage Forms

In one embodiment, solid, anhydrous oral dosage forms can be used. In another aspect, provided herein are transdermal, topical, and mucosal dosage forms. Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, $16^{th}$, $18^{th}$ and $20^{th}$ eds., Mack Publishing, Easton Pa. (1980, 1990 & 2000); and *Introduction to Pharmaceutical Dosage Forms*, $4^{th}$ ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are non toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$, $18^{th}$ and $20^{th}$ eds., Mack Publishing, Easton Pa. (1980, 1990 & 2000).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Methods of Treating or Preventing Disease in a Subject

The compounds disclosed herein, for example, the compounds of formula (I) can act on enzymes called cyclophilins and inhibit their catalytic activity. Accordingly, in another aspect, provided herein are methods to inhibit cyclophilins comprising administering a compound or composition disclosed herein, for example, a compound of formula (I), or a composition comprising a compound of formula (I), to a subject in need thereof. Cyclophilins occur in a wide variety of different organisms, including human, yeast, bacteria, protozoa, metazoa, insects, plants, or viruses. In the case of infectious organisms, inhibition of the cyclophilin catalytic activity by compounds of the present invention often results in an inhibitory effect on the organism. Furthermore, in humans the catalytic activity of cyclophilins plays a role in many different disease situations. Inhibition of this catalytic activity is often associated to a therapeutic effect. Therefore, certain compounds described herein can be used for the treatment of infections including those caused by HCV and HIV (described further below) as well as those caused by fungal pathogens, protozoan and metazoan parasites. In addition, certain compounds disclosed herein can be used to treat neurodegenerative diseases such as Alzheimer's disease, Parkinson's disease, and neuropathies. Another use of the compounds disclosed herein is protection against tissue damage associated with ischemia and reperfusion, such as paralytic damage after spinal cord or head injuries, or cardiac damage after myocardial infarct. Furthermore, the compounds disclosed herein can induce regenerative processes such as that of hair, liver, gingiva, or nerve tissue damaged or lost due to injury or other underlying pathologies, such as damage of the optical nerve in glaucoma.

Certain compounds disclosed herein can be used to treat chronic inflammatory and autoimmune diseases. As immunosuppressants, certain compounds disclosed herein are useful when administered for the prevention of immune-mediated tissue or organ graft rejection. The regulation of the immune response by certain compounds disclosed herein would also find utility in the treatment of autoimmune diseases, such as rheumatoid arthritis, systemic lupus erythematosis, hyperimmunoglobulin E, Hashimoto's thyroiditis, multiple sclerosis, progressive systemic sclerosis, myasthenia gravis, type I diabetes, uveitis, allergic encephalomyelitis, glomerulonephritis. Further uses include the treatment and prophylaxis of inflammatory and hyperproliferative skin diseases and cutaneous manifestations of immunologically-mediated illnesses, such as psoriasis, atopic dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, multiple myeloma, etc.; obstructive airway diseases, which includes conditions such as COPD, asthma (for example, bronchial asthma, allergic asthma, intrinsic asthma, extrinsic asthma and dust asthma), particularly chronic or inveterate asthma (for example, late asthma and airway hyper-responsiveness), bronchitis, allergic rhinitis, and the like; inflammation of mucosa and blood vessels such as gastric ulcers, vascular damage caused by ischemic diseases and thrombosis. Moreover, hyperproliferative vascular diseases such as intimal smooth muscle cell hyperplasia, restenosis and vascular occlusion, particularly following biologically- or mechanically-mediated vascular injury can be treated or prevented by the certain compounds disclosed herein. Other treatable conditions would include but are not limited to ischemic bowel diseases; inflammatory bowel diseases, necrotizing enterocolitis, intestinal lesions associated with thermal burns and leukotriene B4-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastro-intestinal tract (e.g., migraine, rhinitis and eczema); renal diseases such as interstitial nephritis, Goodpasture's syndrome, hemolytic-uremic syndrome and diabetic nephropathy; nervous diseases such as multiple myositis, Guillain-Barre-syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction); intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarring and corneal alkali burn; dermatitis, such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-C4 release; Behcet's disease such as intestinal-, vasculo- or neuro-Behcet's disease, and also Behcet's disease which affects the oral cavity, skin, eye, vulva, articulation, epididymis, lung, kidney and so on. Furthermore, certain compounds disclosed herein are useful for the treatment and prevention of hepatic disease such as immunogenic diseases (for example, chronic autoimmune liver diseases such as the group consisting of autoimmune hepatitis, primary biliary cirrhosis and sclerosing cholangitis), partial liver resection, acute liver necrosis, cirrhosis (such as alcoholic cirrhosis) and hepatic failure such as fulminant hepatic failure, late-onset hepatic failure and acute liver failure on chronic liver diseases.

In one embodiment the invention provides a method of treating or preventing an inflammatory or immune disorder in a subject comprising the administration to the subject of a compound of general formula (I) above in which A and B are as defined above, $R^1$ represents hydrogen, $R^2$ represents —C(=O)$R^{21}$ and $R^{21}$ represents straight- or branched-chain alkyl having from one to three carbon atoms or n-butyl, or a pharmaceutically acceptable salt or solvate thereof. In one aspect of this embodiment $R^2$ represents —C(=O)$R^{21}$ and $R^{21}$ represents straight- or branched-chain alkyl having from one to three carbon atoms (e.g., methyl). In another aspect of this embodiment A represents (E) —CH=CHCH$_3$, B represents ethyl, $R^1$ represents hydrogen, $R^2$ represents —C(=O)$R^{21}$ and $R^{21}$ represents straight-chain alkyl having from one to four carbon atoms. The compounds of this method are novel and form a further embodiment of this invention.

It will be understood that for compounds of formula (I) above which possess immunosuppressive properties may not be suitable for the treatment of immunocompromised patients (e.g., patients with HIV or AIDS).

Methods of Treating or Preventing HCV and/or HIV Infection in a Subject

The present invention provides methods of using a compound or composition disclosed herein, for example, a compound of formula (I), or a composition comprising a compound of formula (I), for the treatment or prevention of a viral infection in a subject in need thereof. The methods generally comprise the step of administering to the subject an effective amount of the compound or composition to treat or prevent the viral infection. In certain embodiments, the viral infection is an HCV infection or an HIV infection, or an HCV and HIV co-infection.

In certain embodiments, the subject can be any subject infected with, or at risk for infection with, HCV. Infection or risk for infection can be determined according to any technique deemed suitable by the practitioner of skill in the art. In certain embodiments, subjects are humans infected with HCV.

The HCV can be any HCV known to those of skill in the art. There are at least six genotypes and at least 50 subtypes of HCV currently known to those of skill in the art. The HCV can be of any genotype or subtype known to those of skill. In certain embodiments, the HCV is of a genotype or subtype not yet characterized. In certain embodiments, the subject is infected with HCV of a single genotype. In certain embodiments, the subject is infected with HCV of multiple subtypes or multiple genotypes.

In certain embodiments, the HCV is genotype 1 and can be of any subtype. For instance, in certain embodiments, the HCV is subtype 1a, 1b or 1c. It is believed that HCV infection of genotype 1 responds poorly to current interferon therapy. Methods of the present invention can be advantageous for therapy of HCV infection with genotype 1.

In certain embodiments, the HCV is other than genotype 1. In certain embodiments, the HCV is genotype 2 and can be of any subtype. For instance, in certain embodiments, the HCV is subtype 2a, 2b or 2c. In certain embodiments, the HCV is genotype 3 and can be of any subtype. For instance, in certain embodiments, the HCV is subtype 3a, 3b or 10a. In certain embodiments, the HCV is genotype 4 and can be of any subtype. For instance, in certain embodiments, the HCV is subtype 4a. In certain embodiments, the HCV is genotype 5 and can be of any subtype. For instance, in certain embodiments, the HCV is subtype 5a. In certain embodiments, the HCV is genotype 6 and can be of any subtype. For instance, in certain embodiments, the HCV is subtype 6a, 6b, 7b, 8b, 9a or 11a. See, e.g., Simmonds, 2004, *J Gen Virol.* 85: 3173-88; Simmonds, 2001, *J. Gen. Virol.* 82: 693-712, the contents of which are herein incorporated by reference in their entireties.

In certain embodiments, the subject has never received therapy or prophylaxis for an HCV infection. In further embodiments, the subject has previously received therapy or prophylaxis for an HCV infection. For instance, in certain embodiments, the subject has not responded to HCV therapy. Indeed, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for HCV infection but has failed show a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding. Since the compounds disclosed herein act by mechanism other than current HCV therapy, it is believed these compounds should be effective in treating such nonresponders.

In certain embodiments, the subject is a subject that discontinued HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, the present invention provides methods of treating or preventing HCV infection in subjects where the risk of neuropsychiatric events, such as depression, contraindicates treatment with current HCV therapy. The present invention also provides methods of treating or preventing HCV infection in subjects where a neuropsychiatric event, such as depression, or risk of such indicates discontinuation of treatment with current HCV therapy. The present invention further provides methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects include bone marrow suppression, neutropenia and thrombocytopenia. Furthermore, ribavirin is toxic to red blood cells and is associated with hemolysis. Accordingly, the present invention also provides methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments the subject has received HCV therapy and discontinued that therapy prior to administration of a method of the invention. In further embodiments, the subject has received therapy and continues to receive that therapy along with administration of a method of the invention. The methods of the invention can be co-administered with other therapy for HCV according to the judgment of one of skill in the art. In advantageous embodiments, the methods or compositions of the invention can be co-administered with a reduced dose of the other therapy for HCV.

In certain embodiments, the present invention provides methods of treating a subject that is refractory to treatment with interferon. For instance, in some embodiments, the subject can be a subject that has failed to respond to treatment with one or more agents selected from the group consisting of interferon, interferon α, pegylated interferon α, interferon plus ribavirin, interferon α plus ribavirin and pegylated interferon α plus ribavirin. In some embodiments, the subject can be a subject that has responded poorly to treatment with one or more agents selected from the group consisting of interferon, interferon α, pegylated interferon α, interferon plus ribavirin, interferon α plus ribavirin and pegylated interferon α plus ribavirin.

In further embodiments, the present invention provides methods of treating HCV infection in subjects that are pregnant or might get pregnant since current therapy is also contraindicated in pregnant women.

In certain embodiments, the methods or compositions of the invention are administered to a subject following liver transplant. Hepatitis C is a leading cause of liver transplantation in the U.S., and many subjects that undergo liver transplantation remain HCV positive following transplantation. The present invention provides methods of treating such recurrent HCV subjects with a compound or composition disclosed herein. In certain embodiments, the present invention provides methods of treating a subject before, during or following liver transplant to prevent recurrent HCV infection.

Cyclosporine compounds of general formula (I) can be particularly useful in the prophylaxis and treatment of retrovirus diseases and more particularly of AIDS and of syndromes associated with AIDS. Prophylaxis is understood to mean in particular the treatment of subjects who have been exposed to HIV viruses, in particular asymptomatic seropositives who present the risk of developing the disease in the months or years to come after the primary infection. In this aspect the cyclosporine compounds of general formula (I) according to the invention can display an anti-retrovirus activity at concentrations devoid of any cytotoxic or cytostatic effect.

In certain embodiments of the invention, the subject can be any subject infected with, or at risk for infection with, HIV. Infection or risk for infection can be determined according to any technique deemed suitable by the practitioner of skill in the art. In certain embodiment, subjects are humans infected with HIV. The HIV can be any HIV known to those of skill in the art.

In certain embodiments of the invention, the subject has never received therapy or prophylaxis for HIV infection. In further embodiments of the invention, the subject has previously received therapy or prophylaxis for HIV infection. For instance, in certain embodiments, the subject has not responded to HIV therapy. In certain embodiments, the subject can be a subject that received therapy but continued to suffer from viral infection or one or more symptoms thereof. In certain embodiments, the subject can be a subject that received therapy but failed to achieve a sustained virologic response.

In certain embodiments, the subject is a subject that has discontinued HIV therapy because of one or more adverse events associated with the therapy. In certain embodiments, the subject is a subject where current therapy is not indicated. In certain embodiments the subject has received HIV therapy and discontinued that therapy prior to administration of a method of the invention. In further embodiments, the subject has received therapy and continues to receive that therapy along with administration of a method of the invention. The methods of the invention can be co-administered with other therapy for HIV according to the judgment of one of skill in the art. In advantageous embodiments, the methods or compositions of the invention can be co-administered with a reduced dose of the other therapy for HIV.

In certain embodiments, the present invention provides methods of treating a subject that is refractory to treatment for HIV. For instance, in some embodiments, the subject can be a subject that has failed to respond to treatment with one or more therapeutic agents for HIV. In some embodiments, the subject can be a subject that has responded poorly to treatment with one or more therapeutic agents for HIV.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8: 577-57. The methods of the invention can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J. Infect. Dis.* 179: 1254-1258. Advantageously, compounds of the invention have been shown to suppress HIV in HIV subjects. See, e.g., U.S. Pat. Nos. 5,977,067, 5,994,299, 5,948,884, and 6,583,265, and International Patent Publication Nos. WO99/32512 and WO99/67280, the contents of which are hereby incorporated by reference in their entireties. Thus, in certain embodiments, the present invention provides methods of treating or preventing HIV infection and HCV infection in subjects in need thereof.

Dosage and Unit Dosage Forms

In human therapeutics, the doctor will determine the posology which he considers most appropriate according to a preventive or curative treatment and according to the age, weight, stage of the infection and other factors specific to the subject to be treated. Generally, doses are from about 1 to about 1500 mg per day for an adult, from about 50 to about 1300 mg per day, or from about 100 to 1100 mg per day for an adult. In one embodiment, dose rates are from about 250 to about 1000 mg per day.

In further aspects, the present invention provides methods of treating or preventing HIV and/or HCV infection in a subject by administering, to a subject in need thereof, an effective amount of a compound disclosed herein, or a pharmaceutically acceptable salt thereof, with a high therapeutic index against HIV and/or HCV. The therapeutic index can be measured according to any method known to those of skill in the art, such as the method described in the examples below. In certain embodiments, the therapeutic index is the ratio of a concentration at which the compound is toxic, to the concentration that is effective against HIV and/or HCV. Toxicity can be measured by any technique known to those of skill including cytotoxicity (e.g., $IC_{50}$ or $IC_{90}$) and lethal dose (e.g., $LD_{50}$ or $LD_{90}$). Likewise, effective concentrations can be measured by any technique known to those of skill including effective concentration (e.g., $EC_{50}$ or $EC_{90}$) and effective dose (e.g., $ED_{50}$ or $ED_{90}$). In certain embodiments, similar measurements are compared in the ratio (e.g., $IC_{50}/EC_{50}$, $IC_{90}/EC_{90}$, $LD_{50}/ED_{50}$ or $LD_{90}/ED_{90}$). In certain embodiments, the therapeutic index can be as high as 2.0, 5.0, 10.0, 15.0, 20.0, 25.0, 50.0, 75.0, 100.0, 125.0, 150.0 or higher.

The amount of the compound or composition of the invention which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For the certain compositions disclosed herein, the dosage administered to a subject is typically about 0.140 mg/kg to about 3 mg/kg of the subject's body weight, based on weight of the active compound. In certain aspects, the dosage administered to a subject is between about 0.20 mg/kg and about 2.00 mg/kg, or between about 0.30 mg/kg and about 1.50 mg/kg of the subject's body weight.

In general, the recommended daily dose range of a composition disclosed herein for the conditions described herein lie within the range of from about 0.1 mg to about 1500 mg per day, given as a single once-a-day dose or as divided doses throughout a day. In one embodiment, the daily dose is administered twice daily in equally divided doses. Specifically, a daily dose range should be from about 50 mg to about 1300 mg per day, more specifically, between about 100 mg and about 1100 mg per day, or even more specifically between about 250 and about 1000 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition of the invention are also encompassed by the above described dosage amounts and dose frequency schedules. Further, when a subject is administered multiple dosages of a composition disclosed herein, not all of the dosages need be the same. For example, the dosage administered to the subject may be increased to improve the prophylactic or therapeutic effect of the composition or it may be decreased to reduce one or more side effects that a particular subject is experiencing.

In a specific embodiment, the dosage of a composition disclosed herein, or of a composition disclosed herein, based on weight of the active compound, which is administered to prevent, treat, manage, or ameliorate a disorder, or one or more symptoms thereof in a subject, is about 0.1 mg/kg, about 1 mg/kg, about 2 mg/kg, about 3 mg/kg, about 4 mg/kg, about 5 mg/kg, about 6 mg/kg, about 10 mg/kg, or about 15 mg/kg or more of a subject's body weight. In another embodiment, the dosage of a composition disclosed herein, or of a composition disclosed herein which is administered to prevent, treat, manage, or ameliorate a disorder, or one or more symptoms thereof in a subject, is a unit dose of about 0.1 mg to about 200 mg, about 0.1 mg to about 100 mg, about 0.1 mg to about 50 mg, about 0.1 mg to about 25 mg, about 0.1 mg to about 20 mg, about 0.1 mg to about 15 mg, about 0.1 mg to about 10 mg, about 0.1 mg to about 7.5 mg, about 0.1 mg to about 5 mg, about 0.1 to about 2.5 mg, about 0.25 mg to about 20 mg, about 0.25 to about 15 mg, about 0.25 to about 12 mg, about 0.25 to about 10 mg, about 0.25 mg to about 7.5 mg, about 0.25 mg to about 5 mg, about 0.5 mg to about 2.5 mg, about 1 mg to about 20 mg, about 1 mg to about 15 mg, about 1 mg to 1 about 2 mg, about 1 mg to about 10 mg, about 1 mg to about 7.5 mg, about 1 mg to about 5 mg, or about 1 mg to about 2.5 mg.

In certain embodiments, treatment or prevention can be initiated with one or more loading doses of a compound or composition disclosed herein followed by one or more maintenance doses. In such embodiments, the loading dose can be, for instance, about 60 to about 400 mg per day, or about 100 to about 200 mg per day, for one day to forty-eight weeks, or from one day to five weeks. The loading dose can be followed by one or more maintenance doses. Each maintenance dose can be, independently, from about 5 mg to about 1500 mg per day, or from about 10 mg to about 200 mg per day, more specifically, between about 25 mg and about 150 mg per day, or even more specifically between about 25 and about 80 mg per day. In certain embodiments, maintenance doses are administered daily and can be administered as single doses, or as divided doses.

In certain embodiments, a dose of a compound or composition disclosed herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition disclosed herein is administered to achieve a steady-state concentration in blood or serum of the subject of from about 300 to about 4000 ng/mL, from about 400 to about 1600 ng/mL, or from about 600 to about 1200 ng/mL. Loading doses can be administered to achieve steady-state blood or serum concentrations of about 1200 to about 8000 ng/mL, or about 2000 to about 4000 ng/mL for one to five days. Maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, the present invention provides unit dosages comprising a compound disclosed herein, or a pharmaceutically acceptable salt thereof, in a form suitable for administration. Such forms are described in detail above. In certain embodiments, the unit dosage comprises about 1 to about 1500 mg, about 5 to about 250 mg or about 10 to about 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

Combination Therapy

The present invention provides methods of treatment of prevention that comprise the administration of a second agent effective for the treatment or prevention of HIV and/or HCV infection in a subject in need thereof. The second agent can be any agent known to those of skill in the art to be effective for the treatment or prevention of the HIV and/or HCV infection. The second agent can be a second agent presently known to those of skill in the art, or the second agent can be second agent later developed for the treatment or prevention of HIV and/or HCV. In certain embodiments, the second agent is presently approved for the treatment or prevention of HIV and/or HCV.

In certain embodiments, a compound disclosed herein is administered in combination with one second agent. In further embodiments, a second agent is administered in combination with two second agents. In still further embodiments, a second agent is administered in combination with two or more second agents.

Suitable second agents include small-molecule, orally bioavailable inhibitors of the HCV enzymes, nucleic-acid-based agents that attack viral RNA, agents that can modulate the host immune response. Exemplary second agents include: (i) current approved therapies (peg-interferon plus ribavirin), (ii) HCV-enzyme targeted compounds, (iii) viral-genome-targeted therapies (e.g., RNA interference or RNAi), and (iv) immunomodulatory agents such as ribavirin, interferon (INF) and Toll-receptor agonists.

In certain embodiments, the second agent is a modulator of the NS3-4A protease. The NS3-4A protease is a heterodimeric protease, comprising the amino-terminal domain of the NS3 protein and the small NS4A cofactor. Its activity is essential for the generation of components of the viral RNA replication complex.

One useful NS3-4A protease inhibitor is BILN 2061 (Ciluprevir; Boehringer Ingelheim), a macrocyclic mimic of peptide product inhibitors. Although clinical trials with BILN 2061 were halted (preclinical cardiotoxicity), it was the first NS3 inhibitor to be tested in humans. See Lamarre et al., 2003, *Nature* 426: 186-189, the content of which is hereby incorporated by reference in its entirety.

Another useful NS3-4A protease inhibitor is VX-950 (Vertex/Mitsubishi), a protease-cleavage-product-derived peptidomimetic inhibitor of the NS3-4A protease. It is believed to be stabilized into the enzyme's active site through a ketoamide. See, e.g., Lin et al., 2005, *J Biol Chem.* Manuscript M506462200 (epublication); Summa, 2005, *Curr Opin Investig Drugs.* 6: 831-7, the contents of which are hereby incorporated by reference in their entireties.

In certain embodiments, the second agent is a modulator of the HCV NS5B The RNA-dependent RNA polymerase (RdRp). Contained within the NS5B protein, RdRp synthesizes RNA using an RNA template. This biochemical activity is not present in mammalian cells.

One useful modulator of RdRp is NM283 (Valopicitabine; Idenix/Novartis). NM283, is an oral prodrug (valine ester) of NM107 (2'-C-methyl-cytidine) in phase II trials for the treatment or prevention of HCV infection. See, e.g., U.S. Patent Application Publication No. 20040077587, the content of which is hereby incorporated by reference in its entirety.

Other useful modulators of RdRp include 7-deaza nucleoside analogs. For instance, 7-Deaza-2'-C-methyl-adenosine is a potent and selective inhibitor of hepatitis C virus replication with excellent pharmacokinetic properties. Olsen et al., 2004, *Antimicrob. Agents Chemother.* 48: 3944-3953, the content of which is hereby incorporated by reference in its entirety.

In further embodiments, the second agent is a non-nucleoside modulator of NS5B. At least three different classes of non-nucleoside inhibitors (NNI) of NS5B inhibitors are being evaluated in the clinic.

Useful non-nucleoside modulators of NS5B include JTK-003 and JTK-009. JTK-003 has been advanced to phase II. Useful non-nucleoside modulators of NS5B include the 6,5-fused heterocyclic compounds based on a benzimidazole or indole core. See, e.g., Hashimoto et al., WO 00147883, the content of which is hereby incorporated by reference in its entirety.

Further useful polymerase NNIs include R803 (Rigel) and HCV-371, HCV-086 and HCV-796 (ViroPharma/Wyeth). Additional useful NNIs include thiophene derivatives that are reversible allosteric inhibitors of the NS5B polymerase and bind to a site that is close to, but distinct from, the site occupied by benzimidazole-based inhibitors. See, e.g., Biswal, et al., 2005, *J. Biol. Chem.* 280: 18202-18210.

Further useful NNIs for the methods of the invention include benzothiadiazines, such as benzo-1,2,4-thiadiazines. Derivatives of benzo-1,2,4-thiadiazine have been shown to be highly selective inhibitors of the HCV RNA polymerase. Dhanak, et al., 2002, *J. Biol. Chem.* 277: 38322-38327, the content of which is hereby incorporated by reference in its entirety.

Further useful NNIs for the methods of the invention, and their mechanisms, are described in LaPlante et al., 2004 *Angew Chem. Int. Ed. Engl.* 43: 4306-4311; Tomei et al., 2003, *J. Virol.* 77: 13225-13231; Di Marco et al., 2005, *J. Biol. Chem.* 280: 29765-70; Lu, H., WO 2005/000308; Chan et al., 2004, *Bioorg. Med. Chem. Lett.* 14: 797-800; Chan et al., 2004, *Bioorg. Med. Chem. Lett.* 14: 793-796; Wang et al., 2003, *J. Biol. Chem.* 278: 9489-9495; Love, et al., 2003, *J. Virol.* 77: 7575-7581; Gu et al., 2003, *J. Biol. Chem.* 278: 16602-16607; Tomei et al., 2004, *J. Virol.* 78: 938-946; and Nguyen et al., 2003, *Antimicrob. Agents Chemother.* 47: 3525-3530; the contents of which are hereby incorporated by reference in their entireties.

In a further embodiment, the second agent is an agent that is capable of interfering with HCV RNA such as small inhibitory RNA (siRNA) or a short hairpin RNA (shRNA) directed to an HCV polynucleotide. In tissue culture, siRNA and vector-encoded short hairpin RNA shRNA directed against the viral genome, effectively block the replication of HCV replicons. See, e.g., Randall et al., 2003, *Proc. Natl Acad. Sci. USA* 100: 235-240, the content of which is hereby incorporated by reference in its entirety.

In a further embodiment, the second agent is an agent that modulates the subject's immune response. For instance, in certain embodiments, the second agent can be a presently approved therapy for HCV infection such as an interferon (IFN), a pegylated IFN, an IFN plus ribavirin or a pegylated IFN plus ribavirin. In certain embodiments, the interferons include IFNα, IFNα2a and IFNα2b, and particularly pegylated IFNα2a (PEGASYS®) or pegylated IFNα2b (PEG-INTRON®).

In a further embodiment, the second agent is a modulator of a Toll-like receptor (TLR). It is believed that TLRs are targets for stimulating innate anti-viral response. Suitable TLRs include, but are not limited to, TLR3, TLR7, TLR8 and TLR9. It is believed that toll-like receptors sense the presence of invading microorganisms such as bacteria, viruses and parasites. They are expressed by immune cells, including macrophages, monocytes, dendritic cells and B cells. Stimulation or activation of TLRs can initiate acute inflammatory responses by induction of antimicrobial genes and pro-inflammatory cytokines and chemokines.

In certain embodiments, the second agent is a polynucleotide comprising a CpG motif. Synthetic oligonucleotides containing unmethylated CpG motifs are potent agonists of TLR-9. Stimulation of dendritic cells with these oligonucleotides results in the production of tumour necrosis factor-alpha, interleukin-12 and IFN-alpha. TLR-9 ligands are also potent stimulators of B-cell proliferation and antibody secretion. One useful CpG-containing oligonucleotide is CPG-10101 (Actilon; Coley Pharmaceutical Group) which has been evaluated in the clinic.

Another useful modulator of a TLR is ANA975 (Anadys). ANA975 is believed to act through TLR-7, and is known to elicit a powerful anti-viral response via induction and the release of inflammatory cytokines such as IFN-alpha.

In another embodiment, the second agent is Celgosivir. Celgosivir is an alpha-glucosidase I inhibitor and acts through host-directed glycosylation. In preclinical studies, celgosivir has demonstrated strong synergy with IFNα plus ribavirin. See, e.g., Whitby et al., 2004, *Antivir Chem Chemother.* 15(3): 141-51. Celgosivir is currently being evaluated in a Phase II monotherapy study in chronic HCV patients in Canada.

Further immunomodulatory agents, and their mechanisms or targets, are described in Schetter & Vollmer, 2004, *Curr. Opin. Drug Discov. Dev.* 7: 204-210; Takeda et al., 2003, *Annu. Rev. Immunol.* 21: 335-376; Lee et al., 2003, *Proc. Natl Acad. Sci. USA* 100: 6646-6651; Hosmans et al., 2004, *Hepatology* 40 (Suppl. 1), 282A; and U.S. Pat. No. 6,924,271; the contents of which are hereby incorporated by reference in their entireties.

In certain embodiments, the present invention provides methods of administering a compound of formula (I) in combination with a second agent effective for the treatment or prevention of HIV infection. The second agent can be any agent known to those of skill in the art to be effective for the treatment of HIV infection. The second agent can be presently known or later developed.

In certain embodiments, the second agent of the invention can be formulated or packaged with the compounds of formula (I). Of course, the second agent will only be formulated with a compound of formula (I) when, according to the judgment of those of skill in the art, such co-formulation should not interfere with the activity of either agent or the method of administration. In certain embodiment, the compound of formula (I) and the second agent are formulated separately. They can be packaged together, or packaged separately, for the convenience of the practitioner of skill in the art.

The dosages of the second agents are to be used in the combination therapies of the invention. In certain embodiments, dosages lower than those which have been or are currently being used to prevent or treat HCV infection are used in the combination therapies of the invention. The recommended dosages of second agents can obtained from the knowledge of those of skill. For those second agents that are approved for clinical use, recommended dosages are described in, for example, Goodman & Gilman's *The Pharmacological Basis Of Basis Of Therapeutics* 9th ed., Hardman et al., eds., Mc-Graw-Hill, New York (1996); *Physician's Desk Reference (PDR)* 57th ed., Medical Economics Co., Inc., Montvale, N.J. (2003), the contents of which are hereby incorporated by reference in their entireties.

In various embodiments, the therapies (e.g., the compound of formula (I) and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to about 18 hours apart, at about 18 hours to about 24 hours apart, at about 24 hours to about 36 hours apart, at about 36 hours to about 48 hours apart, at about 48 hours to about 52 hours apart, at about 52 hours to about 60 hours apart, at about 60 hours to about 72 hours apart, at about 72 hours to about 84 hours apart, at about 84 hours to about 96 hours apart, or at about 96 hours to about 120 hours part. In certain embodiments, two or more therapies are administered within the same patent visit.

In certain embodiments, the compound of formula (I) and the second agent are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound of formula (I) and a second agent are administered to a patient, for example, a mammal such as a human, in a sequence and within a time interval such that the compound of formula (I) can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the compound of formula (I) and the second active agent exert their effect at times which overlap. Each second active agent can be administered separately, in any appropriate form and by any suitable route. In other embodiments, the compound of formula (I) is administered before, concurrently or after administration of the second active agent.

In various embodiments, the compound of formula (I) and the second agent are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other embodiments, the compound of formula (I) and the second agent are administered concurrently.

In other embodiments, the compound of formula (I) and the second agent are administered at about 2 to 4 days apart, at about 4 to 6 days apart, at about 1 week part, at about 1 to 2 weeks apart, or more than 2 weeks apart.

In certain embodiments, the compound of formula (I) and the second agent are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound of formula (I) and the second active agent are administered in a cycle of less than about 3 weeks, about once every two weeks, about once every 10 days or about once every week. One cycle can comprise the administration of a compound of formula (I) and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound of formula (I) can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound of formula (I). In one embodiment, a compound of formula (I) is administered concurrently with one or more second agents in the same pharmaceutical composition. In another embodiment, a compound of formula (I) is administered concurrently with one or more second agents in separate pharmaceutical compositions. In still another embodiment, a compound of formula (I) is administered prior to or subsequent to administration of a second agent. The invention contemplates administration of a compound of formula (I) and a second agent by the same or different routes of administration, e.g., oral and parenteral. In certain embodiments, when a compound of formula (I) is administered concurrently with a second agent that potentially produces adverse side effects including, but not limited to, toxicity, the second active agent can advantageously be administered at a dose that falls below the threshold that the adverse side effect is elicited.

Kits

The invention also provides kits for use in methods of treatment or prophylaxis of HIV and/or HCV infection. The kits can include a pharmaceutical compound or composition disclosed herein and instructions providing information to a health care provider regarding usage for treating or preventing a bacterial infection. Instructions may be provided in printed form or in the form of an electronic medium such as a floppy disc, CD, or DVD, or in the form of a website address where such instructions may be obtained. A unit dose of a compound or composition disclosed herein can include a dosage such that when administered to a subject, a therapeutically or prophylactically effective plasma level of the compound or composition can be maintained in the subject for at least 1 day. In some embodiments, a compound or composition disclosed herein can be included as a sterile aqueous pharmaceutical composition or dry powder (e.g., lyophilized) composition. In one embodiment, the compound is according to formula (I).

In some embodiments, suitable packaging is provided. As used herein, "packaging" refers to a solid matrix or material customarily used in a system and capable of holding within fixed limits a compound or composition disclosed herein suitable for administration to a subject. Such materials include glass and plastic (e.g., polyethylene, polypropylene, and polycarbonate) bottles, vials, paper, plastic, and plastic-foil laminated envelopes, and the like. If e-beam sterilization techniques are employed, the packaging should have sufficiently low density to permit sterilization of the contents.

Kits of the invention may also comprise, in addition to the compound or composition disclosed herein, second agents or compositions comprising second agents for use with the compound or composition as described in the methods above.

The following Examples illustrate the synthesis of representative compounds of formula (I) used in the present invention and the following Reference Examples illustrate the synthesis of intermediates in their preparation. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLE 1

Sodium methoxide (25% by weight, 2.5 Molar equivalents) in methanol was added to a solution of [3'-acetoxy-N-methyl-Bmt]$^1$[2'-methoxy-Sar]$^3$[4'-acetoxy-N-methylleucine]$^4$cyclosporine A (275 mg) in methanol and the resulting mixture stirred at room temperature for 24 hours. Acetic acid was then added to neutralize the excess amount of sodium methoxide. Methanol was removed under reduced pressure and the residue purified using preparative chromatography to yield [(R)-methoxy-Sar]³[4'-acetoxy-N-methylleucine]⁴cyclosporine A (Compound A). ¹H NMR peaks at 5.83, 7.13, 7.74 and 7.89 ppm.

By proceeding in a similar manner the following compounds were prepared:

| Cpd | Name | ¹H NMR (ppm, NH) | LC-MS |
|---|---|---|---|
| B | [(R)-methylthio-Sar]³[4'-N,N'-dimethylaminoacetoxy-N-methylleucine]⁴-cyclosporine A | 5.75, 7.15, 7.45, 7.63, 8.02 | 1350.8 (M + 2) |
| C | [4'-N,N'-dimethylaminoacetoxy-N-methylleucine]⁴cyclosporine A | 7.13, 7.56, 7.59, 7.90 | 1304.8 (M + 2) |
| D | [4'-N'N'-diethylaminoacetoxy-N-methylleucine]⁴cyclosporine A | 7.14, 7.54, 7.61, 7.92 | 677.5 (M + 1 + Na)/2 |

EXAMPLE 2

A solution of a mixture of [4'-hydroxy-N-methylleucine]⁴cyclosporine A (200 mg) and acetic anhydride (0.035 mL) in dichloromethane was treated with bismuth(III) trifluoromethanesulfonate tetrahydrate (5.2 mg) and the resulting mixture was stirred at room temperature over 2.5 days. The crude product was purified by chromatography using a silica gel column to yield [4'-acetoxy-N-methylleucine]⁴cyclosporine A (Compound E). ¹H NMR peaks at 7.14, 7.51, 7.61 and 7.89 ppm; LC MS 631.0 (M+2)/2.

By proceeding in a similar manner the following compounds were prepared:

[4'-trimethylacetoxy-N-methylleucine]⁴cyclosporine A (Compound F). ¹H NMR (400 MHz, CDCl₃) of pertinent peaks δ ppm 0.71 (d, J=5.91 Hz, 3 H), 1.12 (s, 9 H), 2.70 (s, 3 H), 2.71 (s, 3 H), 3.11 (s, 3 H), 3.17 (s, 3 H), 3.26 (s, 3 H), 3.51 (s, 3 H), 3.78 (m, 1 H), 4.00 (m, 1 H), 4.54 (m, 1 H), 4.66 (m, 2 H), 483 (m, 1 H), 4.97 (m, 1 H), 5.06 (m, 2 H), 5.14 (d, J=10.84 Hz, 1 H), 5.34 (m, 2 H), 5.44 (m, 1 H), 5.50 (d, 5.95 Hz, 1 H), 5.70 (dd, J=10.81, 4.08 Hz, 1 H), 7.14 (d, J=7.91 Hz, 1 H), 7.53 (d, J=8.25 Hz, 1 H), 7.58 (d, J=7.57 Hz, 1 H), 7.94 (d, J=9.76 Hz, 1 H); LCMS-MS (ESI+) 663.0 (M+Na+H)/2.

[4'-propionyloxy-N-methylleucine]⁴cyclosporine A (Compound G). ¹H NMR (400 MHz, CDCl₃) δ ppm 0.71 (d, J=5.76 Hz, 3 H), 2.70 (s, 3 H), 2.71 (s, 3H), 3.11 (s, 3 H), 3.14 (s, 3 H), 3.26 (s, 3 H), 3.40 (s, 3 H), 3.51 (s, 3 H), 3.78 (m, 1 H), 4.03 (m, 1 H), 4.54 (m, 1 H), 4.66 (m, 2 H), 4.83 (m, 1 H), 4.96 (dd, J=9.18, 6.49 Hz, 1 H), 5.06 (m, 2 H), 5.14 (d, J=10.88 Hz, 1 H), 5.34 (m, 2 H), 5.49 (m, 2 H), 5.70 (dd, J=10.93, 4.07 Hz, 1 H), 7.13 (d, J=7.91 Hz, 1 H), 7.50 (d, J=8.25 Hz, 1 H), 7.58 (d, J=7.52 Hz, 1 H), 7.90 (d, J=9.71 Hz, 1 H); LCMS-MS (ESI+) 1275.0 (M+H).

[4'-butyryloxy-N-methylleucine]⁴cyclosporine A (Compound H). ¹H NMR (400 MHz, CDCl₃) δ ppm 0.71 (d, J=5.76 Hz, 3 H), 2.70 (s, 3 H), 2.71 (s, 3 H), 3.13 (s, 3 H), 3.15 (s, 3 H), 3.26 (s, 3 H), 3.40 (s, 3 H), 3.51 (s, 3 H), 3.78 (m, 1 H), 4.03 (m, 1 H), 4.54 (m, 1 H), 4.66 (m, 2 H), 4.83 (m, 1 H), 4.96 (dd, J=9.22, 6.39 Hz, 1 H), 5.06 (m, 2 H), 5.14 (d, J=10.83 Hz, 1 H), 5.34 (m, 2 H), 5.49 (m, 2 H), 5.70 (dd, J=10.69, 3.95 Hz, 1 H), 7.14 (d, J=7.86 Hz, 1 H), 7.51 (d, J=8.30 Hz, 1 H), 7.59 (d, J=7.52 Hz, 1 H), 7.91 (d, J=9.66 Hz, 1 H); LCMS-MS (ESI+) 1289.0 (M+H).

[4'-isobutyryloxy-N-methylleucine]⁴cyclosporine A (Compound I). ¹H NMR (400 MHz, CDCl₃) δ ppm 0.71 (d, J=5.71 Hz, 3 H), 2.70 (s, 3 H), 2.71 (s, 3 H), 3.11 (s, 3 H), 3.16 (s, 3 H), 3.26 (s, 3 H), 3.39 (s, 3 H), 3.51 (s, 3 H), 3.78 (m, 1 H), 4.02 (m, 1 H), 4.54 (m, 1 H), 4.66 (m, 2 H), 4.83 (m, 1 H), 4.96 (dd, J=9.22 6.44 Hz, 1 H), 5.06 (m, 2 H), 5.14 (d, J=10.83 Hz, 1 H), 5.34 (m, 2 H), 5.49 (m, 2 H), 5.70 (dd, J=10.64, 3.90 Hz, 1 H), 7.13 (d, J=7.91 Hz, 1 H), 7.52 (d, J=8.44 Hz, 1 H), 7.59 (d, J=7.47 Hz, 1 H), 7.92 (d, J=9.71 Hz, 1 H); LCMS-MS (ESI+) 1288.7 (M+H).

[4'-(trans-2-methyl-2-butenoyl)oxy-N-methylleucine]⁴ cyclosporine A (Compound J). ¹H NMR (400 MHz, CDCl₃) δ ppm 0.70 (d, J=5.95 Hz, 3 H), 2.70 (s, 3 H), 2.71 (s, 3 H), 3.08 (s, 3 H), 3.10 (s, 3 H), 3.26 (s, 3 H), 3.36 (s, 3 H). )s, 3 H), 3.51 (s, 3 H), 3.76 (m, 1 H), 4.19 (m, 1 H), 4.57 (m, 2 H), 4.66 (m, 1 H), 4.83 (m, 1 H), 4.96 (dd, J=9.03, 6.54 Hz, 1 H), 5.06 (m, 2 H), 5.14 (d, J=10.83 Hz, 1 H), 5.34 (m, 2 H), 5.50 (m, 2 H), 5.70 (dd, J=10.64, 3.90 Hz, 1 H), 6.70 (m, 1 H), 7.12 (d, J=7.86 Hz, 1 H), 7.47 (d, J=8.30 Hz, 1 H), 7.56 (d, J=7.52 Hz, 1 H), 7.85 (d, J=9.76 Hz, 1 H); LCMS-MS (ESI+) 1300.7 (M+H).

EXAMPLE 3

[4'-Hydroxy-N-methylleucine]⁴cyclosporine A (210 mg, 0.172 mmol), triethylamine (0.144 mL, 1.03 mmol) and 4-dimethylaminopyridine (126 mg, 1.03 mmol) were dissolved in dry dichloromethane at 0° C. Bis(4-nitrophenyl) carbonate (157 mg, 0.52 mmol) was added, and the mixture was stirred for 30 minutes. The cold bath was removed and the reaction stirred at room temperature for 36 hours. The mixture was diluted with water and extracted with dichloromethane. The organic layer was washed with brine, dried (sodium sulfate), filtered and concentrated with silica gel. Purification by flash column chromatography eluting with 0-100% of a gradient mixture of 10% methanol/ethyl acetate in heptane afforded [4'-hydroxy-N-methylleucine]⁴cyclosporine A p-nitrophenyl 4'-carbonate (Compound K) as an orange solid. ¹H NMR (400 MHz, CDCl₃) δ ppm 0.72 (d, J=5.71 Hz, 3 H), 2.70 (s, 3 H), 2.71 (s, 3 H), 3.12 (s, 3 H), 3.18 (s, 3 H), 3.26 (s, 3 H), 3.39 (s, 3 H), 3.80 (m, 1 H), 4.54 (m, 1 H), 4.70 (m, 2 H), 4.84 (m, 1 H), 4.98 (dd, J=9.27, 6.35 Hz, 1 H), 5.07 (m, 2 H), 5.13 (d, J=10.88 Hz, 1 H), 5.34 (m, 2 H), 5.49 (m, 1 H), 5.59 (m, 1 H), 5.70 (dd, J=10.74, 4.00 Hz, 1 H), 7.15 (d, J=7.86 Hz, 1 H), 7.34 (d, J=9.08 Hz, 2 H), 7.59 (d, J=8.44 Hz, 1 H), 7.64 (d, J=7.52 Hz, 1 H), 7.96 (d, J =9.66 Hz, 1 H) 8.27 (d, J=9.08 Hz, 2 H); LCMS-MS (ESI+) 1383.9 (M+H).

EXAMPLE 4

[4'-Hydroxy-N-methylleucine]⁴cyclosporine A p-nitrophenyl 4'-carbonate (Compound K) (80mg, 0.059 mmol) was dissolved in of dry THF. The vessel was evacuated and refilled with argon, and then triethylamine (0.040 mL, 0.289 mmol) was added followed by dimethylamine (0.145 mL, 0.289 mmol). The reaction mixture, which immediately turned yellow, was stirred at room temperature for 30 minutes. Silica gel was added and the solvent evaporated. Purification by flash column chromatography eluting with 0-100% of a gradient mixture of 5% methanol/ethylacetate in heptane yielded [4'-hydroxy-N-methylleucine]⁴cyclosporine A N,N-dimethyl-4'-carbamate (Compound L) as a white solid. ¹H NMR (400 MHz, CDCl₃) δ ppm 0.70 (d, J=5.91 Hz, 3 H), 2.70 (s, 3 H), 2.71 (s, 3 H), 2.78 (s, 3 H), 2.82 (s, 3 H), 3.10 (s, 3 H), 3.14 (s, 3 H), 3.26 (s, 3 H), 3.39 (s, 3 H), 3.51 (s, 3 H), 3.77 (m, 1 H), 4.28 (d, 6.39 Hz, 1 H), 4.55 (m, 1 H), 4.66 (m, 2 H), 4.83 (m, 1 H), 4.93 (dd, J=8.93, 6.64 Hz, 1 H), 5.06 (m, 2 H), 5.14 (d, J=10.83 Hz, 1 H), 5.34 (m, 2 H), 5.47 (d, J=8.88 Hz, 1 H), 5.52 (d, J=5.76 Hz, 1 H), 5.70 (dd, J=10.64, 3.90 Hz, 1 H), 7.12 (d, J=7.91 Hz, 1 H), 7.48 (d, J=8.20 Hz, 1 H), 7.55 (d, J=7.56 Hz, 1 H), 7.86 (d, J=9.71 Hz, 1 H); LCMS-MS (ESI+) 1289.7 (M+H).

By proceeding in a similar manner the following compounds were prepared:

[4'-hydroxy-N-methylleucine]$^4$cyclosporine A N,N-diethyl-4'-carbamate (Compound M). $^1$H NMR (400 MHz, CDCl$_3$) δ ppm 2.63 (s, 3 H), 2.63 (s, 3 H), 3.03 (s, 3 H), 3.08 (s, 3 H), 3.19 (s, 3 H), 3.31 (s, 3 H), 3.44 (s, 3 H), 7.05 (d, 1 H), 7.42 (d, 1 H), 7.48 (d, 1 H), 7.81 (d, 1 H); LCMS-MS (ESI+) 1317.4 (M+H), 1339.4 (M+Na).

[4'-hydroxy-N-methylleucine]$^4$cyclosporine A N-methyl-4'-carbamate (Compound N). $^1$H NMR (400 MHz, CDCl$_3$) δ ppm 2.61 (d, 3 H), 2.63 (s, 3 H), 2.63 (s, 3 H), 3.03 (s, 3 H), 3.08 (s, 3 H), 3.19 (s, 3 H), 3.33 (s, 3 H), 3.44 (s, 3 H), 7.06 (d, 1 H), 7.42 (d, 1 H), 7.49 (d, 1 H), 7.81 (d, 1 H); LCMS-MS (ESI+) 1275.4 (M+H), 1297.4 (M+Na).

[4'-hydroxy-N-methylleucine]$^4$cyclosporine A N-ethyl-4'-carbamate (Compound O). $^1$H NMR (400 MHz, CDCl$_3$) δ ppm 2.62 (s, 3 H), 2.63 (s, 3 H), 3.03 (s, 3 H), 3.07 (s, 3 H), 3.18 (s, 3 H), 3.32 (s, 3 H), 3.44 (s, 3 H), 7.06 (d, 1 H), 7.42 (d, 1 H), 7.50 (d, 1 H), 7.82 (d, 1 H); LCMS-MS (ESI+) 1289.4 (M+H), 1311.4 (M+Na).

[4'-hydroxy-N-methylleucine]$^4$cyclosporine A N-allyl-4'-carbamate (Compound P). $^1$H NMR (400 MHz, CDCl$_3$) δ ppm 2.63 (s, 3 H), 2.63 (s, 3 H), 3.03 (s, 3 H), 3.07 (s, 3 H), 3.18 (s, 3 H), 3.32 (s, 3 H), 3.44 (s, 3 H), 5.68-5.77 (m, 1H), 7.06 (d, 1 H), 7.43 (d, 1 H), 7.52 (d, 1 H), 7.81 (d, 1 H); LCMS-MS (ESI+) 1301.4 (M+H), 1323.4 (M+Na).

[4'-hydroxy-N-methylleucine]$^4$cyclosporine A N-(n-butyl)-4'-carbamate (Compound Q). $^1$H NMR (400 MHz, CDCl$_3$) δ ppm 2.63 (s, 3 H), 2.63 (s, 3 H), 3.03 (s, 3 H), 3.08 (s, 3 H), 3.18 (s, 3 H), 3.32 (s, 3 H), 3.44 (s, 3 H), 7.06 (d, 1 H), 7.42 (d, 1 H), 7.52 (d, 1 H), 7.82 (d, 1 H); LCMS-MS (ESI+) 1317.4 (M+H), 1339.4 (M+Na).

[4'-hydroxy-N-methylleucine]$^4$cyclosporine A N-(n-hexyl)-4'-carbamate (Compound R). $^1$H NMR (400 MHz, CDCl$_3$) δ ppm 2.63 (s, 3 H), 2.63 (s, 3 H), 3.03 (s, 3 H), 3.07 (s, 3 H), 3.18 (s, 3 H), 3.32 (s, 3 H), 3.44 (s, 3 H), 7.06 (d, 1 H), 7.42 (d, 1 H), 7.51 (d, 1 H), 7.82 (d, 1 H); LCMS-MS (ESI+) 1345.4 (M+H), 1367.4 (M+Na).

[4'-hydroxy-N-methylleucine]$^4$cyclosporine A N-benzyl-4'-carbamate (Compound S). $^1$H NMR (400 MHz, CDCl$_3$) δ ppm 2.62 (s, 3 H), 2.63 (s, 3 H), 3.01 (s, 3 H), 3.03 (s, 3 H), 3.17 (s, 3 H), 3.20 (s, 3 H), 3.43 (s, 3 H), 7.05 (d, 1 H), 7.18-7.28 (m, 5H), 7.41 (d, 1 H), 7.49 (d, 1 H), 7.78 (d, 1 H); LCMS-MS (ESI+) 1351.4 (M+H), 1373.4 (M+Na).

[4'-hydroxy-N-methylleucine]$^4$cyclosporine A N-(p-methoxybenzyl)-4'-carbamate (Compound T). $^1$H NMR (400 MHz, CDCl$_3$) δ ppm 2.62 (s, 3 H), 2.63 (s, 3 H), 3.02 (s, 3H), 3.03 (s, 3 H), 3.17 (s, 3 H), 3.21 (s, 3 H), 3.43 (s, 3 H), 3.72 (s, 3H), 6.77-6.81 (m, 2H), 7.05 (d, 1 H), 7.11-7.13 (m, 2H), 7.42 (d, 1 H), 7.49 (d, 1 H), 7.78 (d, 1H); LCMS-MS (ESI+) 1381.4 (M+H), 1403.5 (M+Na).

[4'-hydroxy-N-methylleucine]$^4$cyclosporine A azetidine-4'-carbamate (Compound U). $^1$H NMR (400 MHz, CDCl$_3$) δ ppm 2.63 (s, 3 H), 2.63 (s, 3 H), 3.03 (s, 3 H), 3.07 (s, 3 H), 3.18 (s, 3 H), 3.34 (s, 3 H), 3.44 (s, 3 H), 7.05 (d, 1 H), 7.41 (d, 1 H), 7.48 (d, 1 H), 7.81 (d, 1 H); LCMS-MS (ESI+) 1301.4 (M+H), 1323.4 (M+Na).

[4'-hydroxy-N-methylleucine]$^4$cyclosporine A pyrrolidine-4'-carbamate (Compound V). $^1$H NMR (400 MHz, CDCl$_3$) δ ppm 2.63 (s, 3 H), 2.64 (s, 3 H), 3.03 (s, 3 H), 3.08 (s, 3H), 3.19 (s, 3 H), 3.31 (s, 3 H), 3.44 (s, 3 H), 7.05 (d, 1 H), 7.40 (d, 1 H), 7.49 (d, 1 H), 7.80 (d, 1 H); LCMS-MS (ESI+) 1315.4 (M+H), 1337.4 (M+Na).

[4'-hydroxy-N-methylleucine]$^4$cyclosporine A piperidine-4'-carbamate (Compound W). $^1$H NMR (400 MHz, CDCl$_3$) δ ppm 2.63 (s, 3 H), 2.63 (s, 3 H), 3.03 (s, 3 H), 3.06 (s, 3H), 3.19 (s, 3 H), 3.32 (s, 3 H), 3.44 (s, 3 H), 7.05 (d, 1 H), 7.41 (d, 1 H), 7.49 (d, 1 H), 7.82 (d, 1 H); LCMS-MS (ESI+) 1329.4 (M+H), 1351.4 (M+Na).

[4'-hydroxy-N-methylleucine]$^4$cyclosporine A S-benzyl-4'-thiocarbonate (Compound X). $^1$H NMR (400 MHz, CDCl$_3$) δ ppm 2.62 (s, 3 H), 2.63 (s, 3 H), 2.90 (s, 3 H), 3.03 (s, 3H), 3.17 (s, 3 H), 3.25 (s, 3 H), 3.43 (s, 3 H), 7.05 (d, 1 H), 7.17-7.28 (m, 5H), 7.45 (d, 1 H), 7.52 (d, 1 H), 7.77 (d, 1 H); LCMS-MS (ESI+) 1368.4 (M+H), 1390.4 (M+Na).

[4'-hydroxy-N-methylleucine]$^4$cyclosporine A 4-methyl-1-piperazine-4'-carbamate (Compound Y). $^1$H NMR (400 MHz, CDCl$_3$) δ ppm 2.21 (s, 3H), 2.62 (s, 3 H), 2.63 (s, 3 H), 3.03 (s, 3 H), 3.06 (s, 3H), 3.18 (s, 3 H), 3.32 (s, 3 H), 3.44 (s, 3 H), 7.05 (d, 1 H), 7.43 (d, 1 H), 7.49 (d, 1 H), 7.83 (d, 1 H); LCMS-MS (ESI+) 1344.4 (M+H).

[4'-hydroxy-N-methylleucine]$^4$cyclosporine A N,N-dimethylethylenediamine-4'-carbamate (Compound Z). $^1$H NMR (400 MHz, CDCl$_3$) δ ppm 2.13 (s, 6H), 2.62 (s, 3 H), 2.63 (s, 3 H), 3.03 (s, 3 H), 3.07 (s, 3H), 3.18 (s, 3 H), 3.32 (s, 3 H), 3.44 (s, 3 H), 7.06 (d, 1 H), 7.42 (d, 1 H), 7.51 (d, 1 H), 7.83 (d, 1 H); LCMS-MS (ESI+) 1332.5 (M+H).

REFERENCE EXAMPLE 1

Camphor sulfonic acid was added to a solution of [3'-acetoxy-N-methyl-Bmt]$^1$[2'-acetoxy-Sar]$^3$[4'-acetoxy-N-methylleucine]$^4$cyclosporine A (130 mg) in methanol (2 mL), and the resulting mixture was stirred at 50° C. for 5 hours. The reaction mixture was diluted with ethyl acetate, washed with saturated sodium hydrogen carbonate and brine, and then concentrated to yield [3'-acetoxy-N-methyl-Bmt]$^1$[(R)-methoxy-Sar]$^3$-[4'-acetoxy-N-methylleucine]$^4$ cyclosporine A. $^1$H NMR showed a sarcosine proton at 5.65 ppm.

REFERENCE EXAMPLE 2

Mercury acetate (100 mg) was added to a solution of [3'-acetoxy-N-methyl-Bmt]$^1$ [2'-thiophenyl-Sar]$^3$-[4'-acetoxy-N-methylleucine]$^4$cyclosporine A (100 mg) in glacial acetic acid and the resulting mixture was stirred for 3 hours at 50° C. The solvent was then removed and the residue dissolved in ethyl acetate, washed with a saturated solution of sodium hydrogen carbonate and then brine, and dried over sodium sulphate. After removal of the solvent, the final product was analyzed by $^1$H NMR and yielded [3'-acetoxy-N-methyl-Bmt]$^1$[2'-acetoxy-Sar]$^3$-[4'-acetoxy-N-methylleucine]$^4$-cyclosporine A.

REFERENCE EXAMPLE 3

N,N-Dimethylaminopyridine (310 mg), tetraethylammonium bromide (0.35 mg) and acetic anhydride (0.16 mL) were added to a solution of [2'-thiophenyl-Sar]$^3$-[4'-hydroxy-N-methylleucine]$^4$cyclosporine A (550 mg) in dry dichloromethane. The resulting mixture was stirred at room temperature for about 2.5 days. The reaction mixture was then diluted with ethyl acetate, washed with water and brine and concentrated. The crude product was purified by chromatography using a silica gel column, eluting with a mixture of ethyl acetate and hexane to yield [3'-acetoxy-N-methyl-Bmt]$^1$[2'-thiophenyl-Sar]$^3$-[4'-acetoxy-N-methylleucine]$^4$ cyclosporine A.

REFERENCE EXAMPLE 4

A solution of [4'-hydroxy-N-methylleucine]$^4$cyclosporine A (1.22 g) in dry t-butyl methyl ether (TBME) was added to a suspension of sodium amide (1.0 g) in liquid ammonia (30 mL) at −33° C. under inert atmosphere. The resulting mixture was stirred at −33° C. for 90 minutes under an inert atmosphere. Phenyl disulfide (4.4 g) was then added, and the reaction mixture was stirred for an additional 2 hours at −33° C. under an inert atmosphere. The reaction mixture was then diluted with TBME and water, mixed thoroughly, and the layers separated. The organic layer was washed with brine and then concentrated. The residue was purified by chromatography using a silica gel column eluting first with a mixture of ethyl acetate and heptane, and then with a mixture of methanol and ethyl acetate, to yield [2'-thiophenyl-Sar]$^3$-[4'-hydroxy-N-methylleucine]$^4$cyclosporine A.

REFERENCE EXAMPLE 5

Potassium iodide (20 mg, 1.1 equivalents), di-isopropylethylamine (0.02 mL, 1.1 equivalents), and dimethylamine (0.06 mL, 2.0 M solution in THF, 1.1 equivalents) were added to a solution of [3'-acetoxy-N-methyl-Bmt]$^1$[2'-methylthio-Sar]$^3$ [4'-chloroacetoxy-N-methylleucine]$^4$cyclosporine A (100 mg) in dry acetonitrile and the resulting mixture was stirred at room temperature for 40 hours. The reaction mixture was diluted with water and extracted with ethyl acetate. The combined organic extracts were washed with brine and then concentrated. The crude product was purified by chromatography using a silica gel column, eluting with ethyl acetate in heptane to yield [3'-acetoxy-N-methyl-Bmt]$^1$[2'-methylthio-Sar]$^3$-[4'-N'N-dimethylaminoacetoxy-N-methylleucine]$^4$cyclosporine A.

By proceeding in a similar manner [3'-acetoxy-N-methyl-Bmt]$^1$[4'-N'N-dimethylaminoacetoxy-N-methylleucine]$^4$cyclosporine A and [3'-acetoxy-N-methyl-Bmt]$^1$ [4'-N'N-diethylaminoacetoxy-N-methylleucine]$^4$cyclosporine A were also prepared.

REFERENCE EXAMPLE 6

Chloroacetic anhydride (120 mg, 10 equivalents) and pyridine (0.06 mL, 10 equivalents) were added to a solution of [3'-acetoxy-N-methyl-Bmt]$^1$[2'-methylthio-Sar]$^3$-[4'-hydroxy-N-methylleucine]$^4$cyclosporine A (90 mg) in dichloromethane containing 4-dimethylaminopyridine (0.01 g, 1.0 equivalent) and the resulting mixture was stirred for 5 hours at room temperature. A second batch of chloroacetic anhydride (0.05 g, 5.0 equivalents) and pyridine (0.03 mL, 5.0 equivalents) were added and the reaction mixture was stirred for 12 hours. A third batch of chloroacetic anhydride (0.05 g, 5.0 equivalents) and pyridine (0.03 mL, 5.0 equivalents) were added and the reaction mixture was stirred for 12 hours followed by the addition of the final batch of chloroacetic anhydride (0.05 g, 5.0 equivalents) and pyridine (0.03 mL, 5.0 equivalents) and the reaction mixture was stirred for another 12 hours. The reaction mixture was diluted with ethyl acetate and water and the layers were separated. The organic layer was washed with cold 1.0 N hydrochloric acid in water, saturated sodium bicarbonate in water, brine, and dried over anhydrous sodium sulphate. After removal of the solvent, the residue was purified by chromatography using a silica gel column eluting with ethyl acetate and heptane to yield [3'-acetoxy-N-methyl-Bmt]$^1$[2'-methylthio-Sar]$^3$-[4'-chloroacetoxy-N-methylleucine]$^4$cyclosporine A.

By proceeding in a similar manner [3'-acetoxy-N-methyl-Bmt]$^1$-[4'-chloroacetoxy-N-methylleucine]$^4$cyclosporine A was also prepared.

REFERENCE EXAMPLE 7

Scandium trifluoromethanesulfonate (11 mg, 0.33 equivalents) was added to a solution of [3'-acetoxy-N-methyl-Bmt]$^1$ [2'-methylthio-Sar]$^3$[4'-tert-butyldimethylsiloxy-N-methylleucine]$^4$cyclosporine A (100 mg) in dichloromethane and the resulting mixture stirred at room temperature overnight. The crude reaction mixture was directly loaded onto a 12-gram silica gel cartridge, eluting with ethyl acetate in heptane. Fractions containing the desired product were pooled, concentrated under reduced pressure, and dried under vacuum to yield [3'-acetoxy-N-methyl-Bmt]$^1$ [2'-methylthio-Sar]$^3$[4'-hydroxy-N-methylleucine]$^4$cyclosporine A.

REFERENCE EXAMPLE 8

Acetic anhydride (0.07 mL, 10 equivalents) and 4-dimethylaminopyridine (0.044 g, 5 equivalents) were added to a solution of [2'-methylthio-Sar]$^3$-[4'-tert-butyldimethylsiloxy-N-methylleucine]$^4$cyclosporine A (100 mg) in pyridine and the resulting mixture was stirred for 60 hours at room temperature. The reaction mixture was diluted with ethyl acetate and water and the layers were separated. The organic layer was washed with cold 1.0 N hydrochloric acid in water, saturated sodium bicarbonate in water, brine and dried over anhydrous sodium sulphate. After removal of the solvent, the residue was purified by chromatography using a silica gel column eluting with ethyl acetate and heptane to yield [3'-acetoxy-N-methyl-Bmt]$^1$[2'-methylthio-Sar]$^3$-[4'-tert-butyldimethylsiloxy-N-methylleucine]$^4$cyclosporine A.

REFERENCE EXAMPLE 9

Triethylamine (0.06 mL, 2.2 equivalents) and tert-butyldimethylsilyl trifluoromethanesulfonate (0.05 mL, 1.1 equivalents) were added to a solution of [2'-methylthio-Sar]$^3$-[4'-hydroxy-N-methylleucine]$^4$cyclosporine A (250 mg) in dry dichloromethane. The resulting mixture was stirred at room temperature for about 2.5 hours. The reaction mixture was then concentrated and the crude product was purified by chromatography using a silica gel column, eluting with a mixture of heptane and 5% methanol in ethyl acetate to yield [2'-methylthio-Sar]$^3$-[4'-tert-butyldimethylsiloxy-N-methylleucine]$^4$cyclosporine A.

REFERENCE EXAMPLE 10

A solution of [4'-hydroxy-N-methylleucine]$^4$cyclosporine A (5.0 g) in dry t-butyl methyl ether (TBME) was added to a suspension of sodium amide (4.0 g) in liquid ammonia (125 mL) at −33° C. under an inert atmosphere. The resulting mixture was stirred at −33° C. for 90 minutes under an inert atmosphere. Methyl disulfide (7.7 g) was then added, and the reaction mixture was stirred for an additional 2 hours at −33° C. under an inert atmosphere. The reaction mixture was then diluted with TBME and water, mixed thoroughly and the layers separated. The organic layer was washed with brine and then concentrated. The residue was purified by chromatography using a silica gel column, eluting first with a mixture of ethyl acetate and heptane followed by a mixture of methanol and ethyl acetate, to yield [2'-methylthio-Sar]$^3$-[4'-hydroxy-N-methylleucine]$^4$cyclosporine A.

[4'-Hydroxy-N-methylleucine]$^4$cyclosporine A was prepared according to the method described in European Patent No. 484,281, the disclosure of which is specifically incorporated by reference in its entirety.

HCV Activity

The compounds of formula (I) were tested for activity against HCV using the methods adapted from those described by Kriger et al., 2001, *Journal of Virology* 75: 4614-4624, Pietschmann et al., 2002, *Journal of Virology* 76: 4008-4021, and using HCV RNA constructs as described in U.S. Pat. No. 6,630,343. Compounds were examined in the human hepatoma cell line ET (lub ubi neo/ET), a HCV RNA replicon containing a stable luciferase (LUC) reporter. The HCV RNA replicon ET contains the 5' end of HCV (with the HCV Internal Ribosome Entry Site (IRES) and the first few amino acids of the HCV core protein) which drives the production of a firefly luciferase (LUC), ubiquitin, and neomycin phosphotransferase (NeoR) fusion protein. Ubiquitin cleavage releases the LUC and NeoR proteins. The EMCV IRES element controls the translation of the HCV structural proteins NS3-NS5. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The activity of the LUC reporter is directly proportional to HCV replication levels and positive-control antiviral compounds produce a reproducible antiviral response using the LUC endpoint.

The compounds were dissolved in DMSO at five half-log concentrations each, ranging from either 0.03 to 3 µM or 1 to 100 µM. Subconfluent cultures of the ET line were plated out into 96 well plates dedicated for the analysis of cell numbers (cytotoxicity) or antiviral activity and the next day the compounds were added to the appropriate wells. The cells were processed 72 hours later when the cells were still subconfluent. Antiviral activity was expressed as $EC_{50}$ and $EC_{90}$, the effective concentration of compound that reduced viral replication by 50% and 90%, respectively. Compound $EC_{50}$ and $EC_{90}$ values were derived from HCV RNA levels assessed as HCV RNA replicon derived LUC activity. Cytotoxicity was expressed as $IC_{50}$ and $IC_{90}$, the concentration of compound that inhibited cell viability by 50% and 90%, respectively. Compound $IC_{50}$ and $IC_{90}$ values were calculated using a colorimetric assay as an indication of cell numbers and cytotoxicity. The activity of the LUC reporter is directly proportional to HCV RNA levels in the human cell line. The HCV-replicon assay was validated in parallel experiments using interferon-alpha-2b as a positive control. Cyclosporine was also tested by way of comparison. In certain embodiments, the compounds of formula (I) potently inhibit HCV replication in human liver cells to a greater extent than cyclosporine. In addition, when considering the level of cytotoxicity, in certain embodiments, the compounds of formula (I) exhibit a wider safety margin (antiviral $IC_{50}$ versus cytotoxicity $EC_{50}$) than cyclosporine.

HIV Activity

The compounds of formula (I) are also tested for antiretroviral activity against human immunodeficiency virus-1 (HIV) using infection of the human T-lymphoblastoid cell line, CEM-SS, with the HIV strain HIV-1IIIB (Weislow et al., 1989, *J. Natl. Cancer Inst.* 81: 577-586). In this MTS cytoprotection assay, each experiment included cell control wells (cells only), virus control wells (cells plus virus), drug toxicity wells (cells plus drug only), drug colorimetric control wells (drug only) as well as experimental wells (drug plus cells plus virus). Compounds are first dissolved in DMSO and tested using six half-log dilutions, starting with a high concentration of either 20 or 2 µM. HIV-1RF was added to each well in a volume of the amount of virus determined to give approximately 90% cell killing at 6 days post-infection. At assay termination, assay plates are stained with the soluble tetrazolium-based dye MTS (CellTiter 96 Reagent, Promega) to determine cell viability and quantify compound toxicity. MTS is metabolized by the mitochondria enzymes of metabolically active cells to yield a soluble formazan product, providing a quantitative analysis of cell viability and compound cytotoxicity. The assay is validated in parallel experiments using Zidovudine (3'-azido-3'-deoxythymidine or AZT) as a positive control. The assay includes determinations of compound $EC_{50}$ (concentration inhibiting virus replication by 50%), $IC_{50}$ (concentration resulting in 50% inhibition of cell growth) and a selectivity index ($IC_{50}/EC_{50}$).

Cyclophilin Binding Activity

The cyclophilin inhibition binding of the compounds of formula (I) was determined using a competitive ELISA adapted from the methods described by Quesniaux et al. (Quesniaux et al., 1987, *Eur. J Immunol.* 27: 1359-1365). Activated ester of succinyl spacers bound to D-Lys$^8$-cylosporine A (D-Lys$^8$-Cs) was coupled to bovine serum albumin (BSA) through D-lysyl residue in position 8. BSA was dissolved in 0.1 M borate buffer, pH 9.0 (4 mg in 1.4 ml). A hundredfold molar excess of D-Lys$^8$-Cs dissolved in dimethyl formamide (0.6 ml) was added drop wise to the BSA under vigorous stirring. The coupling reaction was performed for 2 to 3 hours at room temperature under mild stirring and the conjugate was extensively dialyzed against phosphate-buffered saline (PBS, pH 7.4). After acetone precipitation of an aliquot of the conjugated protein, no covalently bound D-Lys$^8$-Cs remained in the acetone solution and the extent of cyclosporine covalent binding was calculated.

Microtiter Plates were coated with D-Lys$^8$-Cs-BSA conjugate (2 pg/ml in PBS for 24 hours at 4° C.). Plates were washed with Tween®/PBS and with PBS alone. To block nonspecific binding, 2% BSA/PBS (pH 7.4) was added to the wells and allowed to incubate for 2 hours at 37° C. A five-fold dilution series of the compound to be tested was made in ethanol in a separate microtiter plate. The starting concentration was 0.1 mg/mL for assays with human recombinant cyclophilin. 198 µL of 0.1 µg/mL cyclophilin solution was added to the microtiter immediately followed by 2 µL of diluted cyclosporine A (used as a reference compound) or a compound disclosed herein. The reaction between coated BSA-Cs conjugate, free cyclosporine A and cyclophilin was allowed to equilibrate overnight at 4° C. Cyclophilin was detected with anti-cyclophilin rabbit antiserum diluted in 1% BSA containing PBS and incubated overnight at 4° C. Plates were washed as described above. Bound rabbit antibodies were then detected by goat anti-rabbit IgG conjugated to alkaline phosphatase diluted in 1% BSA-PBS and allowed to incubate for 2 hours at 37° C. Plates were washed as described above. After incubation with 4-nitrophenyl phosphate (1 g/l in diethanolamine buffer, pH 9.8) for 1 to 2 hours at 37° C., the enzymatic reaction was measured spectrophotometrically at 405 nm using a spectrophotometer. The results were expressed as a cyclophilin binding ratio, which is the $Log_{10}$ difference in the concentrations of the compound disclosed herein and Cyclosporine A each required to achieve 50% inhibition.

The results were as follows: Compounds A to F had cyclophilin A binding ratio of 0.35 or lower and a cyclophilin B binding ratio of 0.21 or lower, illustrating the ability of representative compounds of formula (I) to inhibit cyclophilin.

Compounds of formula (I) were tested for their T Cell stimulation (IL-2) in Jurkat cells with anti-CD3 and anti-CD28 co-stimulation. All compounds had a 0.5-Log 9-point titration starting at 10 µM (n=2) to 0.0015 µM. Cyclosporine A (control) was also run at a 0.5-Log 9-point titration.starting at 500 ng/mL. All compounds to be tested were dissolved in dimethyl sulfoxide. Cytotoxicity was evaluated with parallel Alamar Blue plates. Jurkat cells were seeded at 2×10$^5$ cells per well in 190 µL growth media in a 96-well plate. Cells were cultured in RPMI 1640 medium, 10% fetal bovine serum, and L-Glutamine with incubation at 37° C. with 5% carbon dioxide. After 1 hour of incubation the cells were stimulated with immobilized anti-CD3 (0.4 μg/well), anti-CD28 soluble (2 μg/mL). After 6 hours the sample supernatants were harvested and stored at −80° C. 50 μL samples of supernatant were tested for IL-2 using a Luminex® 1-plex assay.

The following IL-2 activity results were obtained: The $EC_{50}$ value for Compound E was less than 0.01 μM. The $EC_{50}$ values for Compound G and H were less than 0.1 μM. The $EC_{50}$ values for Compounds A and I to L were between 0.1 and 0.9 μM. The $EC_{50}$ values for Compounds B, C and D were greater than 10 μM. The $EC_{50}$ value for cyclosporine A was 2.7 ng/ml. None of the compounds of formula (I) tested displayed cytotoxicity.

Mitochondrial Permeability Transition

Mitochondrial permeability transition (MPT) was determined by measuring swelling of the mitochondria induced by $Ca^{2+}$. The procedure was adapted from the method described by Blattner et al., 2001, *Analytical Biochem.*, 295: 220. Mitochondria were prepared from rat livers, which had been perfused with phosphate-buffered saline (PBS) to remove blood, using standard methods that utilized gentle homogenization in sucrose based buffer and then differential centrifugation to first remove cellular debris and then to pellet the mitochondria. Swelling was induced by 150 micro molar $Ca^{2+}$ (added from a concentrated solution of Calcium chloride) and was monitored by measuring the scattering at 535-540 nm. Representative compounds were added 5 minutes before swelling was induced. $EC_{50}$ were determined by comparing swelling with and without the compounds of formula (I).

In the above test Compounds A to W gave $EC_{50}$ values of 10 μM or lower, indicating the ability of the compounds of formula (I) to penetrate mitochondria and inhibit the MPT. Compound X gave a value of over 30 μM.

All publications and patent applications cited in this specification are herein incorporated by reference in their entireties as if each individual publication or patent application were specifically and individually indicated to be incorporated by reference. While the invention has been described in terms of various embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

The invention claimed is:

1. A compound of general formula (I):

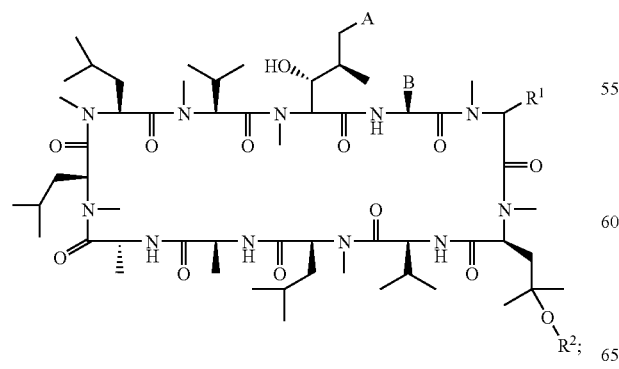

wherein
A is (E) —CH═CHR or —CH$_2$CH$_2$R, wherein R represents methyl, —CH$_2$SH, —CH$_2$(thioalkyl), —CH$_2$(carboxyl), —CH$_2$alkoxycarbonyl, carboxyl or alkoxycarbonyl;
B represents ethyl, 1-hydroxyethyl, isopropyl or n-propyl;
$R^1$ represents hydrogen, lower alkyl, allyl or —XR$^{10}$;
$R^2$ represents —C(═O)R$^{21}$;
X represents —S(═O)$_n$— or oxygen, where n is zero, one or two;
$R^{10}$ represents:
  straight- or branched-chain alkyl having from one to six carbon atoms, optionally substituted by one or more groups $R^3$ which may be the same or different;
  straight- or branched-chain alkenyl having from two to six carbon atoms optionally substituted by one or more substituents which may be the same or different selected from the group consisting of halogen, hydroxy, amino, N-monoalkylamino and N,N-dialkylamino;
  straight- or branched-chain alkynyl having from two to six carbon atoms, optionally substituted by one or more substituents which may be the same or different selected from the group consisting of halogen, hydroxy, amino, N-monoalkylamino and N,N-dialkylamino;
  cycloalkyl containing from three to six carbon atoms optionally substituted by one or more substituents which may be the same or different selected from the group consisting of halogen, hydroxy, amino, N-monoalkylamino and N,N-dialkylamino;
  or straight- or branched-chain alkoxycarbonyl having from two to six carbon atoms;
$R^3$ is selected from the group consisting of halogen; hydroxy; alkoxy; carboxyl; alkoxycarbonyl; —NR$^4$R$^5$, —NR$^6$(CH$_2$)$_m$NR$^4$R$^5$; phenyl optionally substituted by one or more substituents which may be the same or different selected from the group consisting of halogen, alkyl, alkoxy, haloalkyl, cyano, amino, N-alkylamino and N,N-dialkylamino; and a heterocyclic ring which may be saturated or unsaturated containing five or six ring atoms and from one to three heteroatoms which may be the same or different selected from the group consisting of nitrogen, sulfur and oxygen, wherein said heterocyclic ring is attached to alkyl via a ring carbon atom;
$R^4$ and $R^5$, which may be the same or different, each represent:
  hydrogen;
  straight- or branched-chain alkyl having from one to six carbon atoms, optionally substituted by one or more groups $R^7$ which may be the same or different;
  straight- or branched-chain alkenyl or alkynyl having from two to four carbon atoms;
  cycloalkyl containing from three to six carbon atoms optionally substituted by straight- or branched-chain alkyl containing from one to six carbon atoms;
  phenyl optionally substituted by from one to five substituents which may be the same or different selected from the group consisting of halogen, alkoxy, cyano, alkoxycarbonyl, amino, alkylamino and dialkylamino; or
  a heterocyclic ring which may be saturated or unsaturated containing five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four substituents which may be the same or different selected from the group consisting of alkyl, phenyl and benzyl;

$R^6$ represents hydrogen or straight- or branched-chain alkyl having from one to six carbon atoms;

$R^7$ represents halogen, hydroxy, carboxyl, alkoxycarbonyl or —$NR^8R^9$;

$R^8$ and $R^9$ which may be the same or different, each represent hydrogen or straight- or branched-chain alkyl having from one to six carbon atoms;

$R^{21}$ represents:
- hydrogen, or straight- or branched-chain alkyl having from one to six carbon atoms, optionally substituted by one or more groups $R^{22}$ which may be the same or different; straight- or branched-chain alkenyl having from two to six carbon atoms optionally substituted by one or more substituents which may be the same or different selected from the group consisting of halogen, hydroxy, carboxyl, amino, N-monoalkylamino and N,N-dialkylamino;
- straight- or branched-chain alkynyl having from two to six carbon atoms, optionally substituted by one or more substituents which may be the same or different selected from the group consisting of halogen, hydroxy, carboxyl, amino, N-monoalkylamino and N,N-dialkylamino;
- cycloalkyl containing from three to six carbon atoms optionally substituted by one or more substituents which may be the same or different selected from the group consisting of halogen, hydroxy, carboxyl, amino, N-monoalkylamino and N,N-dialkylamino; —$OR^{11}$, —$SR^{11}$, —$NR^{12}R^{13}$;
- aminocarbonyl, N-mono(lower alkyl)aminocarbonyl or N,N-di(lower alkyl)aminocarbonyl;
- phenyl optionally substituted by one or more substituents which may be the same or different selected from the group consisting of halogen, alkyl, alkoxy, haloalkyl, cyano, nitro, amino, N-alkylamino and N,N-dialkylamino;
- or a heterocyclic ring which may be saturated or unsaturated containing from four to six ring atoms and from one to three heteroatoms which may the same or different selected from nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

$R^{11}$ represents:
- straight- or branched-chain alkyl having from one to six carbon atoms, optionally substituted by one or more groups $R^{23}$ which may be the same or different; or
- phenyl optionally substituted by one or more substituents which may be the same or different selected from the group consisting of halogen, alkyl, alkoxy, haloalkyl, cyano, nitro, amino, N-alkylamino and N,N-dialkylamino;

$R^{12}$ and $R^{13}$, which may be the same or different, each represents:
- hydrogen;
- straight- or branched-chain alkyl having from one to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;
- straight- or branched-chain alkenyl having from two to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;
- straight- or branched-chain alkynyl having from two to six carbon atoms optionally substituted by one or more substituents which may be the same or different selected from the group consisting of amino, N-monoalkylamino, N,N-dialkylamino, hydroxy, alkoxy, thioalkyl, carboxy and alkoxycarbonyl;
- phenyl optionally substituted by one or more substituents which may be the same or different selected from the group consisting of halogen, alkyl, alkoxy, haloalkyl, cyano, nitro, amino, N-alkylamino and N,N-dialkylamino; or
- benzyl, wherein the phenyl ring is optionally substituted by one or more substituents which may be the same or different selected from the group consisting of halogen, alkyl, alkoxy, haloalkyl, cyano, nitro, amino, N-alkylamino and N,N-dialkylamino;
- or $R^{12}$ and $R^{13}$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four substituents which may be the same or different selected from the group consisting of alkyl, phenyl and benzyl;

$R^{22}$ and $R^{23}$, which may be the same or different, each represents halogen; hydroxy; alkoxy; carboxyl; alkoxycarbonyl; amino; N-monoalkylamino; N,N-dialkylamino; —$S(\!=\!O)_p$alkyl; —$S(\!=\!O)_p$aryl; cycloalkyl containing from three to six carbon atoms optionally substituted by one or more substituents which may be the same or different selected from the group consisting of halogen, hydroxy, amino, N-monoalkylamino and N,N-dialkylamino; phenyl optionally substituted by one or more substituents which may be the same or different selected from the group consisting of halogen, alkyl, alkoxy, haloalkyl, cyano, amino, N-alkylamino and N,N-dialkylamino; or a heterocyclic ring which may be saturated or unsaturated containing four, five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkyl, alkoxy, haloalkyl, cyano, amino, N-alkylamino and N,N-dialkylamino;

p is zero, one or two;

m is an integer from two to four;

or a pharmaceutically acceptable salt thereof.

2. A compound of general formula (I) defined in claim 1 wherein:

A is (E) —CH=CHR or —CH$_2$CH$_2$R, wherein R represents methyl, —CH$_2$SH, —CH$_2$(thioalkyl), —CH$_2$(carboxyl) or —CH$_2$alkoxycarbonyl;

B represents ethyl, 1-hydroxyethyl, isopropyl or n-propyl;

$R^1$ represents hydrogen, lower alkyl, allyl or —XR$^{10}$;

$R^2$ represents —C(=O)R$^{21}$;

X represents —S(=O)$_n$— or oxygen, where n is zero, one or two;

$R^{10}$ represents:
  straight- or branched-chain alkyl having from one to six carbon atoms, optionally substituted by one or more groups R$^3$ which may be the same or different;
  straight- or branched-chain alkenyl having from two to six carbon atoms optionally substituted by one or more substituents which may be the same or different selected from the group consisting of halogen, hydroxy, amino, N-monoalkylamino and N,N-dialkylamino;
  straight- or branched-chain alkynyl having from two to six carbon atoms, optionally substituted by one or more substituents which may be the same or different selected from the group consisting of halogen, hydroxy, amino, N-monoalkylamino and N,N-dialkylamino;
  cycloalkyl containing from three to six carbon atoms optionally substituted by one or more substituents which may be the same or different selected from the group consisting of halogen, hydroxy, amino, N-monoalkylamino and N,N-dialkylamino;
  or straight- or branched-chain alkoxycarbonyl having from two to six carbon atoms;

$R^3$ is selected from the group consisting of halogen; hydroxy; alkoxy; carboxyl; alkoxycarbonyl; —NR$^4$R$^5$; —NR$^6$(CH$_2$)$_m$NR$^4$R$^5$; phenyl optionally substituted by one or more substituents which may be the same or different selected from the group consisting of halogen, alkyl, alkoxy, haloalkyl, cyano, amino, N-alkylamino and N,N-dialkylamino; and a heterocyclic ring which may be saturated or unsaturated containing five or six ring atoms and from one to three heteroatoms which may be the same or different selected from the group consisting of nitrogen, sulfur and oxygen, wherein said heterocyclic ring is attached to alkyl via a ring carbon atom;

$R^4$ and $R^5$, which may be the same or different, each represent:
  hydrogen;
  straight- or branched-chain alkyl having from one to six carbon atoms, optionally substituted by one or more groups R$^7$ which may be the same or different;
  straight- or branched-chain alkenyl or alkynyl having from two to four carbon atoms;
  cycloalkyl containing from three to six carbon atoms optionally substituted by straight- or branched-chain alkyl containing from one to six carbon atoms;
  phenyl optionally substituted by from one to five substituents which may be the same or different selected from the group consisting of halogen, alkoxy, cyano, alkoxycarbonyl, amino, alkylamino and dialkylamino; or
  a heterocyclic ring which may be saturated or unsaturated containing five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;
  or $R^4$ and $R^5$, together with the nitrogen atom to which they are attached, form a saturated or unsaturated heterocyclic ring containing from four to six ring atoms, which ring may optionally contain another heteroatom selected from the group consisting of nitrogen, oxygen and sulfur and may be optionally substituted by from one to four substituents which may be the same or different selected from the group consisting of alkyl, phenyl and benzyl;

$R^6$ represents hydrogen or straight- or branched-chain alkyl having from one to six carbon atoms;

$R^7$ represents halogen, hydroxy, carboxyl, alkoxycarbonyl or —NR$^8$R$^9$;

$R^8$ and $R^9$ which may be the same or different, each represent hydrogen or straight- or branched-chain alkyl having from one to six carbon atoms;

$R^{21}$ represents:
  hydrogen, or straight- or branched-chain alkyl having from one to six carbon atoms, optionally substituted by one or more groups R$^{22}$ which may be the same or different;
  straight- or branched-chain alkenyl having from two to six carbon atoms optionally substituted by one or more substituents which may be the same or different selected from the group consisting of halogen, hydroxy, carboxyl, amino, N-monoalkylamino and N,N-dialkylamino;
  straight- or branched-chain alkynyl having from two to six carbon atoms, optionally substituted by one or more substituents which may be the same or different selected from the group consisting of halogen, hydroxy, carboxyl, amino, N-monoalkylamino and N,N-dialkylamino;
  cycloalkyl containing from three to six carbon atoms optionally substituted by one or more substituents which may be the same or different selected from the group consisting of halogen, hydroxy, carboxyl, amino, N-monoalkylamino and N,N-dialkylamino;
  aminocarbonyl, N-mono(lower alkyl)aminocarbonyl or N,N-di(lower alkyl)aminocarbonyl;
  phenyl optionally substituted by one or more substituents which may be the same or different selected from the group consisting of halogen, alkyl, alkoxy, haloalkyl, cyano, amino, N-alkylamino and N,N-dialkylamino;
  or a heterocyclic ring which may be saturated or unsaturated containing from four to six ring atoms and from one to three heteroatoms which may the same or different selected from nitrogen, sulfur and oxygen, which heterocyclic ring may be optionally substituted by one or more substituents which may be the same or different selected from the group consisting of halogen, alkoxy, cyano, alkoxycarbonyl, amino, alkylamino and dialkylamino;

$R^{22}$ represents halogen; hydroxy; alkoxy; carboxyl; alkoxycarbonyl; amino; N-monoalkylamino; N,N-dialkylamino; —S(=O)$_p$alkyl; —S(=O)$_p$aryl; cycloalkyl containing from three to six carbon atoms optionally substituted by one or more substituents which may be the same or different selected from the group consisting of halogen, hydroxy, amino, N-monoalkylamino and N,N-dialkylamino; phenyl optionally substituted by one or more substituents which may be the same or different selected from the group consisting of halogen, alkyl, alkoxy, haloalkyl, cyano, amino, N-alkylamino and N,N-dialkylamino; or a heterocyclic ring which may be saturated or unsaturated containing four, five or six ring atoms and from one to three heteroatoms which may the same or different selected from the group consisting of nitrogen, sulfur and oxygen, which heterocyclic ring may be optionally substituted by one or more substituents which may be the same or different selected from the group consisting of halogen, alkyl, alkoxy, haloalkyl, cyano, amino, N-alkylamino and N,N-dialkylamino;

p is zero, one or two;

m is an integer from two to four;

or a pharmaceutically acceptable salt thereof.

3. The compound according to claim 1 in which $R^1$ represents hydrogen or —$XR^{10}$.

4. The compound according to claim 1 in which A represents (E)—CH=CHR, R represents methyl and B represents ethyl.

5. The compound according to claim 1 in which $R^{21}$ represents straight- or branched-chain alkyl having from one to four carbon atoms, optionally substituted by one or more groups $R^{22}$ which may be the same or different.

6. The compound according to claim 1 in which $R^{21}$ represents:

straight- or branched-chain alkyl having from one to six carbon atoms, optionally substituted by one or more groups $R^{22}$ which may be the same or different;

straight- or branched-chain alkenyl having from three to six carbon atoms; or

—$OR^{11}$, —$SR^{11}$, or —$NR^{12}R^{13}$.

7. The compound according to claim 6 in which (a) $R^{11}$ represents:

straight- or branched-chain alkyl having from one to six carbon atoms, optionally substituted by a group $R^{23}$;

or phenyl optionally substituted by one or more substituents which may be the same or different selected from the group consisting of halogen, alkyl, alkoxy, haloalkyl, cyano, nitro, amino, N-alkylamino and N,N-dialkylamino;

(b) $R^{12}$ and $R^{13}$, which may be the same or different, each represents:

hydrogen;

straight- or branched-chain alkyl having from one to six carbon atoms;

straight- or branched-chain alkenyl having from two to six carbon atoms;

benzyl, wherein the phenyl ring is optionally substituted by one or more substituents which may be the same or different selected from the group consisting of halogen, alkyl, alkoxy, haloalkyl, cyano, nitro, amino, N-alkylamino and N,N-dialkylamino;

or $R^{12}$ and $R^{13}$, together with the nitrogen atom to which they are attached, form a saturated heterocyclic ring containing from four to six ring atoms, which ring may optionally contain another heteroatom selected from the group consisting of nitrogen, oxygen and sulfur and may be optionally substituted by one or more alkyl groups which may be the same or different.

8. The compound according to claim 1 which is selected from the group consisting of:

[(R)-methoxy-Sar]$^3$[4'-acetoxy-N-methylleucine]$^4$cyclosporine A;

[(R)-methylthio-Sar]$^3$[4'-N,N'-dimethylaminoacetoxy-N-methylleucine]$^4$-cyclosporine A;

[4'-N,N'-dimethylaminoacetoxy-N-methylleucine]$^4$cyclosporine A;

[4'-N,N'-diethylaminoacetoxy-N-methylleucine]$^4$cyclosporine A;

[4'-acetoxy-N-methylleucine]$^4$cyclosporine A;

[4'-trimethylacetoxy-N-methylleucine]$^4$cyclosporine A;

[4'-propionyloxy-N-methylleucine]$^4$cyclosporine A;

[4'-butyryloxy-N-methylleucine]$^4$cyclosporine A;

[4'-isobutyryloxy-N-methylleucine]$^4$cyclosporine A;

[4'-(trans-2-methyl-2-butenoyl)oxy-N-methylleucine]$^4$ cyclosporine A;

[4'-hydroxy-N-methylleucine]$^4$cyclosporine A p-nitrophenyl-4'-carbonate;

[4'-hydroxy-N-methylleucine]$^4$cyclosporine A N,N-dimethyl-4'-carbamate;

[4'-hydroxy-N-methylleucine]$^4$cyclosporine A N,N-diethyl-4'-carbamate;

[4'-hydroxy-N-methylleucine]$^4$cyclosporine A N-methyl-4'-carbamate;

[4'-hydroxy-N-methylleucine]$^4$cyclosporine A N-ethyl-4'-carbamate;

[4'-hydroxy-N-methylleucine]$^4$cyclosporine A N-allyl-4'-carbamate;

[4'-hydroxy-N-methylleucine]$^4$cyclosporine A N-(n-butyl)-4'-carbamate;

[4'-hydroxy-N-methylleucine]$^4$cyclosporine A N-(n-hexyl)-4'-carbamate;

[4'-hydroxy-N-methylleucine]$^4$cyclosporine A N-benzyl-4'-carbamate;

[4'-hydroxy-N-methylleucine]$^4$cyclosporine A N-(p-methoxybenzyl)-4'-carbamate;

[4'-hydroxy-N-methylleucine]$^4$cyclosporine A azetidine-4'-carbamate;

[4'-hydroxy-N-methylleucine]$^4$cyclosporine A pyrrolidine-4'-carbamate;

[4'-hydroxy-N-methylleucine]$^4$cyclosporine A piperidine-4'-carbamate;

[4'-hydroxy-N-methylleucine]$^4$cyclosporine A S-benzyl-4'-thiocarbonate;

[4'-hydroxy-N-methylleucine]$^4$cyclosporine A 4-methyl-1-piperazine-4'-carbamate; and

[4'-hydroxy-N-methylleucine]$^4$cyclosporine A N,N-dimethylethylenediamine-4'-carbamate.

9. A composition comprising a compound of general formula (I) as defined in claim 1, or a pharmaceutically acceptable salt thereof, and a pharmaceutically acceptable excipient, carrier or diluent.

10. A method of treating Hepatitis C virus infection in a subject, the method comprising administering to the subject a compound of general formula (I) as defined in claim 1, or a pharmaceutically acceptable salt thereof, optionally with a pharmaceutically acceptable excipient, carrier or diluent.

11. A process for the preparation of a compound of formula (I) as defined in claim 1, comprising:

(a) deprotecting a compound of formula (II):

(II)

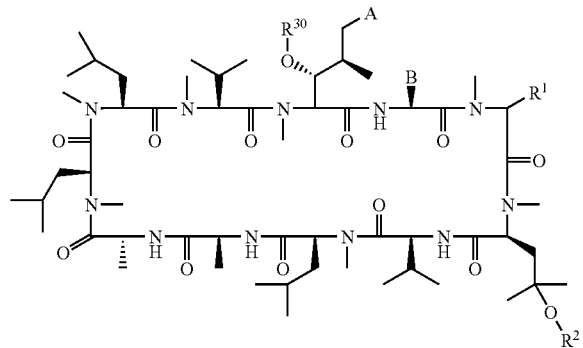

wherein A, B, $R^1$ and $R^2$ are as defined in claim 1 and $R^{30}$ represents a protecting group, to replace the protecting group $R^{30}$ with hydrogen; or (b) reacting a compound of formula (VI):

(VI)

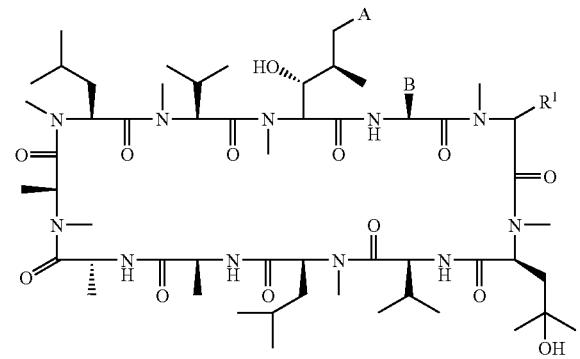

wherein A, B and $R^1$ are as defined in claim 1 with an anhydride of formula $(R^{21}CO)_2O$, wherein $R^{21}$ is as defined in claim 1, in the presence a metal catalyst.

12. A compound of formula (II)

(II)

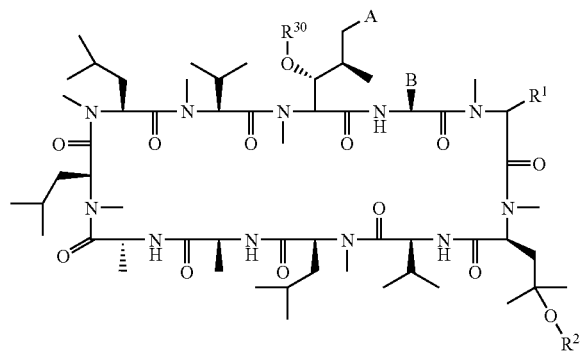

wherein A, B, $R^1$ and $R^2$ are as defined in claim 1 and $R^{30}$ represents a protecting group, wherein when $R^2$ and $R^{30}$ simultaneously represent acetyl, then $R^1$ is other than hydrogen, thiomethyl, methoxy, acetoxy or ethylene-(2,2)-diethylamino.

13. A compound of general formula (III), (IV) or (V):

(III)

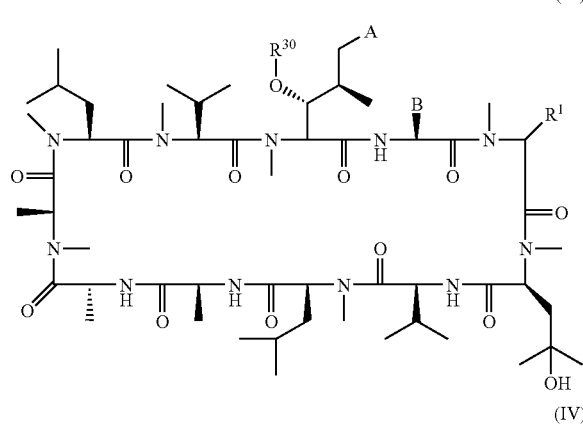

(IV)

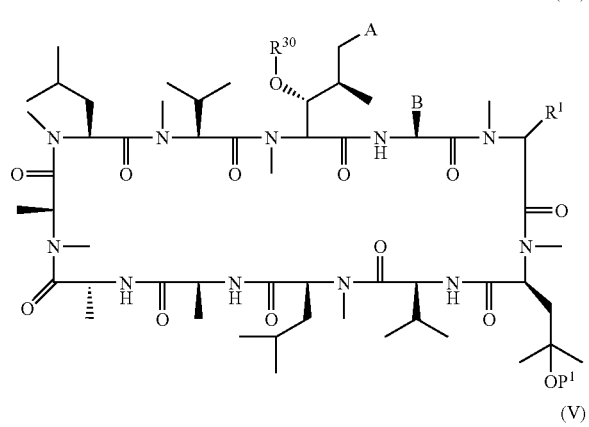

(V)

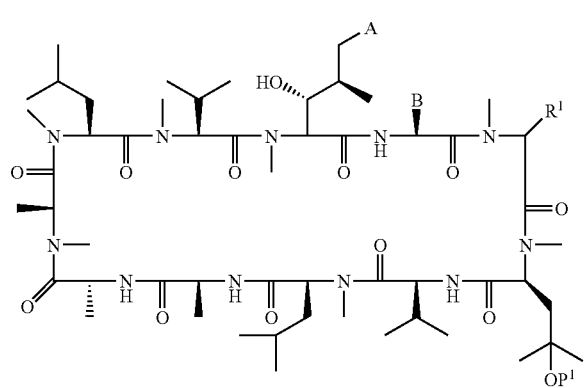

wherein A, B, $R^1$ and $R^2$ as defined in claim 1, $R^{30}$ represents a protecting group, and $P^1$ represents a silyl group.

\* \* \* \* \*